United States Patent
Kim et al.

(10) Patent No.: US 9,629,613 B2
(45) Date of Patent: Apr. 25, 2017

(54) METHOD OF DETERMINING BEAMFORMING COEFFICIENT, BEAMFORMING METHOD AND ULTRASONIC IMAGING APPARATUS

(71) Applicant: SAMSUNG ELECTRONICS CO., LTD., Suwon-si (KR)

(72) Inventors: Kyu Hong Kim, Seongnam-si (KR); Joo Young Kang, Yongin-si (KR); Jung Ho Kim, Yongin-si (KR); Sung Chan Park, Suwon-si (KR); Su Hyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 581 days.

(21) Appl. No.: 14/067,225

(22) Filed: Oct. 30, 2013

(65) Prior Publication Data

US 2014/0121516 A1    May 1, 2014

(30) Foreign Application Priority Data

Oct. 30, 2012  (KR) .................. 10-2012-0120975

(51) Int. Cl.
*G01S 7/52* (2006.01)
*A61B 8/08* (2006.01)
(Continued)

(52) U.S. Cl.
CPC ........ *A61B 8/5207* (2013.01); *G01S 7/52047* (2013.01); *G01S 15/8915* (2013.01);
(Continued)

(58) Field of Classification Search
CPC ..................... G01S 7/52046; G01S 7/52085
See application file for complete search history.

(56) References Cited

U.S. PATENT DOCUMENTS 6,066,099 A    5/2000   Thomenius et al.
6,296,612 B1  10/2001   Mo et al.
(Continued)

FOREIGN PATENT DOCUMENTS

JP       2010-68957 A      4/2010
KR  10-2009-0016666 A      2/2009

*Primary Examiner* — Luke Ratcliffe
*Assistant Examiner* — Hovhannes Baghdasaryan
(74) *Attorney, Agent, or Firm* — Sughrue Mion, PLLC

(57) ABSTRACT

Disclosed herein are a beamforming method, a method of determining a beamforming coefficient, and an ultrasonic imaging apparatus. The beamforming method includes radiating a target object with ultrasonic waves and receiving a plurality of ultrasonic signals reflected from the target object, acquiring beamforming computation results of some of the plurality of received ultrasonic signals and determining a beamforming coefficient candidate group based on a beamforming computation result of the some of the received ultrasonic signals, acquiring beamforming computation results of the plurality of received ultrasonic signals or the some of the received ultrasonic signals by applying beamforming coefficients of the beamforming coefficient candidate group and selecting at least one beamforming coefficient from the beamforming coefficient candidate group based on the beamforming computation results of the plurality of ultrasonic signals, and beamforming the plurality of ultrasonic signals using the selected at least one beamforming coefficient as a weight.

12 Claims, 18 Drawing Sheets

(51) Int. Cl.
  *G10K 11/34* (2006.01)
  *A61B 8/00* (2006.01)
  *G01S 15/89* (2006.01)

(52) U.S. Cl.
  CPC .......... *G10K 11/346* (2013.01); *A61B 8/4405* (2013.01); *A61B 8/4483* (2013.01); *G01S 15/8995* (2013.01); *G01S 15/8997* (2013.01)

(56) References Cited

U.S. PATENT DOCUMENTS

| | | | | |
|---|---|---|---|---|
| 6,490,448 B1 * | 12/2002 | Hogberg | ............ | H04B 7/18543 342/354 |
| 7,254,199 B1 * | 8/2007 | Desloge | ................. | H04B 7/086 375/350 |
| 2012/0271144 A1 * | 10/2012 | Kim | .................... | G01S 7/52047 600/407 |

* cited by examiner

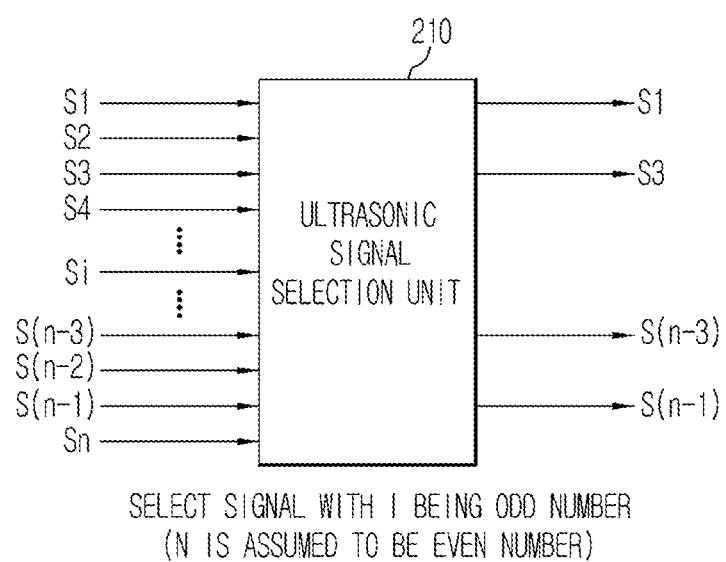

METHOD OF DETERMINING BEAMFORMING COEFFICIENT, BEAMFORMING METHOD AND ULTRASONIC IMAGING APPARATUS

CROSS-REFERENCE TO RELATED APPLICATION(S)

This application claims the benefit of Korean Patent Application No. 2012-0120975, filed on Oct. 30, 2012 in the Korean Intellectual Property Office, the disclosure of which is incorporated herein by reference.

BACKGROUND

1. Field

Embodiments of the present invention relate to a method of determining a beamforming coefficient, a beamforming method, and an ultrasonic imaging apparatus.

2. Description of the Related Art

An ultrasonic imaging apparatus radiates ultrasonic waves toward a target part inside a target object, for example, a human body from a surface of the target object and then collects reflected ultrasonic waves to acquire a sectional image of various tissues or structures inside the target object, for example, an image of blood flow or a sectional image of soft tissue based on information contained in the collected ultrasonic waves.

The ultrasonic imaging apparatus is relatively small in size, inexpensive, displays an image in real time, and has high stability due to no radiation exposure as compared with an X-ray imaging apparatus, and thus, has been extensively used for diagnosis of the heart, abdomen, and urinary system and in obstetrics and gynecology.

In order to acquire an ultrasonic image, the ultrasonic imaging apparatus performs beamforming to estimate the size of reflected waves of a predetermined space from channel data that is collected by an ultrasonic probe from an ultrasonic echo signal. Beamforming is a process of acquiring an image appropriate for diagnosis of a target object by compensating for a time difference of ultrasonic signals input through each ultrasonic sensor, for example, a transducer, applying predetermined weights to respective ultrasonic signals so as to emphasize a signal at a predetermined position and to relatively attenuate a signal at another predetermined position, and focusing ultrasonic signals.

Beamforming of an ultrasonic imaging apparatus may be classified into data-independent beamforming and adaptive beamforming according to the characteristics of weights used in beamforming and applied respective ultrasonic signals (ultrasonic channels).

The data-independent beamforming uses a weight that is determined regardless of an input ultrasonic signal, and is referred to as fixed beamforming since the weight used therein is not changed.

The adaptive beamforming determines an appropriate weight according to an input ultrasonic signal. According to the adaptive beamforming, a weight may be changed according to the input ultrasonic signal. The adaptive beamforming is referred to as data-dependant beamforming.

SUMMARY

Exemplary embodiments of the present invention provide a method of determining a beamforming coefficient, a beamforming method, and an ultrasonic imaging apparatus, for reducing computational load to reduce a period of time of beamforming, reducing resources used for beamforming coefficient computation, and preventing overheating and the like.

In addition, computational load in a process for acquiring beamforming coefficients may be reduced in an adaptive beamforming method.

Additional aspects of the invention will be set forth in part in the description which follows and, in part, will be obvious from the description, or may be learned by practice of the invention.

In accordance with exemplary embodiments of the present invention, a method of determining a beamforming coefficient, a beamforming method, and an ultrasonic imaging apparatus are provided.

In accordance with an exemplary embodiment of the present invention, a method of determining a beamforming coefficient includes selecting some of a plurality of ultrasonic signals reflected from a target object and received (e.g. a first group of ultrasonic signals may be selected), acquiring a plurality of beamforming computation results of the selected ultrasonic signals by applying a plurality of beamforming coefficients, and determining a beamforming coefficient candidate group based on the plurality of beamforming computation results, and acquiring beamforming computation results of the plurality of received ultrasonic signals or the some of the plurality of received ultrasonic signals (e.g. the first group of ultrasonic signals) by applying a beamforming coefficient of the beamforming coefficient candidate group and selecting at least one beamforming coefficient from the beamforming coefficient candidate group based on beamforming computation results of the plurality of ultrasonic signals.

In accordance with another exemplary embodiment of the present invention, a beamforming method includes radiating a target object with ultrasonic waves and receiving a plurality of ultrasonic signals reflected from the target object, acquiring beamforming computation results of some of the plurality of received ultrasonic signals (e.g. a first group of ultrasonic signals) and determining a beamforming coefficient candidate group based on a beamforming computation result of the some of the received ultrasonic signals (e.g. the first group of ultrasonic signals), acquiring beamforming computation results of the plurality of received ultrasonic signals or the some (e.g. the first group) of the received ultrasonic signals by applying beamforming coefficients of the beamforming coefficient candidate group and selecting at least one beamforming coefficient from the beamforming coefficient candidate group based on the beamforming computation results of the plurality of ultrasonic signals, and beamforming the plurality of ultrasonic signals using the selected at least one beamforming coefficient as a weight.

In accordance with another exemplary embodiment of the present invention, a beamforming method includes radiating a target object with ultrasonic waves and receiving a plurality of ultrasonic signals reflected from the target object, acquiring beamforming computation results of some of the plurality of received ultrasonic signals (e.g. a first group of ultrasonic signals) and acquiring a beamforming coefficient candidate group and a plurality of beamforming computation results of the plurality of beamforming coefficients based on the beamforming computation result of the some of the plurality of received ultrasonic signals (e.g. the first group of ultrasonic signals), applying beamforming coefficients of the beamforming coefficient candidate group to acquire beamforming computation results of the plurality of received ultrasonic signals or the some of the plurality of received ultrasonic signals (e.g. the first group of ultrasonic signals), selecting at least one beamforming coefficient from the beamforming coefficient candidate group based on beamforming computation results of the plurality of ultrasonic signals, and acquiring a beamforming computation result of at least one final beamforming coefficient using a plurality of beamforming computation results of the plurality of beamforming coefficients, and beamforming the plurality of ultrasonic signals using the selected at least one final beamforming coefficient as a weight.

In accordance with further exemplary embodiment of the present invention, a beamforming method includes radiating a target object with ultrasonic waves and then receiving a plurality of ultrasonic signals reflected from the target object, determining a beamforming coefficient candidate group with respect to some of the plurality of received ultrasonic signals (e.g. a first group of ultrasonic signals) according to Expression 1 or Expression 2 below, selecting at least one beamforming coefficient from the beamforming coefficient candidate group, and beamforming the plurality of ultrasonic signals using the selected at least one beamforming coefficient as a weight:

$$\{w_c\} = \mathop{\text{argmin}}_{N\text{-best } w_p} \sum_{k=-K_{coarse}}^{k=K_{coarse}} \left| \sum_{i \in A1} w_p[i] x_{n+k}[i] \right|, \quad \text{[Expression 1]}$$

and $$\{w_c\} = \mathop{\text{argmin}}_{N\text{-best } w_p} \sum_{k=-K_{coarse}}^{k=K_{coarse}} \left| \sum_{i \in A1} w_p[i] x_{n+k}[i] \right|^2 \quad \text{[Expression 2]}$$

where $W_c$ is a beamforming coefficient included in the beamforming coefficient candidate group, $W_p[i]$ is a beamforming coefficient, $x_{n+k}[i]$ is an ultrasonic signal, p is a beamforming coefficient index, i is a first channel index, M is the number of reception ultrasonic channels, N is the number of beamforming coefficients included in the beamforming coefficient candidate group, k is an axial smoothing variable, and $K_{coarse}$ is an upper or lower limit of the smoothing variable for acquisition of a plurality of beamforming coefficients for optimization of beamforming computation results of the some of the ultrasonic signals (e.g. the first group of ultrasonic signals).

In this case, the selection of the at least one of beamforming coefficient from the beamforming coefficient candidate group may include selecting at least one beamforming coefficient from the beamforming coefficient candidate group according to Expression 3 or Expression 4 below with respect to the plurality of received ultrasonic signals:

$$\{w_f\} = \mathop{\text{argmin}}_{w_c} \left[ S_c(w_c^{(n)}) + \sum_{k \notin K_{coarse}} \left| \sum_{j \in A2} w_c^{(n)}[j] x_{n+k}[j] \right| \right], \quad \text{[Expression 3]}$$

and $$\{w_f\} = \mathop{\text{argmin}}_{w_c} \left[ S_c(w_c^{(n)}) + \sum_{k \notin K_{coarse}} \left| \sum_{j \in A2} w_c^{(n)}[j] x_{n+k}[j] \right|^2 \right] \quad \text{[Expression 4]}$$

where $W_f$ is the selected beamforming coefficient, j is a second channel index, and $S_c(w^{(n)}_c)$ is a beamforming computation result of an $n_{th}$ coefficient $w^{(n)}_c$ of the determined beamforming coefficient $W_c$.

In accordance with further exemplary embodiments of the present invention, an ultrasonic imaging apparatus includes an ultrasonic probe to radiate a target object with ultrasonic waves, to receive an ultrasonic signal reflected from the target object, and to convert received ultrasonic waves to output a plurality of ultrasonic signals, a beamforming coefficient computation unit to select some of the plurality of output ultrasonic signals (e.g. a first group of ultrasonic signals), to determine a beamforming coefficient candidate group based on a beamforming computation result of the selected ultrasonic signals, and to select at least one beamforming coefficient from the beamforming coefficient candidate group based on beamforming computation results of the plurality of ultrasonic signals, a beamforming unit to perform beamforming on the plurality of ultrasonic signals to output a beamforming computation result using the selected at least one final beamforming coefficient as a weight, and an image processor to form ultrasonic image data based on the beamforming computation result output by the beamforming unit.

The ultrasonic imaging apparatus may further include a beamforming coefficient database including a plurality of beamforming coefficients.

The foregoing general description and the following detailed description are only exemplary and explanatory and they are intended to provide further explanation of the invention as claimed.

BRIEF DESCRIPTION OF THE DRAWINGS

These and/or other aspects and exemplary embodiments of the invention will become apparent and more readily appreciated from the following description of the embodiments, taken in conjunction with the accompanying drawings of which:

FIGS. 8A through 8C are diagrams for explaining selection of ultrasonic waves by an ultrasonic signal selection unit, according to embodiments of the present invention;

DETAILED DESCRIPTION

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art. Descriptions of well-known functions and structures are omitted to enhance clarity and conciseness.

The use of the terms "first", "second", and the like does not imply any particular order, but they are included to identify individual elements. Moreover, the use of the terms first, second, etc. does not denote any order or importance, but rather the terms first, second, etc. are used to distinguish one element from another.

Although some features may be described with respect to individual exemplary embodiments, aspects need not be limited thereto such that features from one or more exemplary embodiments may be combinable with other features from one or more exemplary embodiments.

In order to explaining the embodiments of the present invention with reference to FIGS. 1 to 13, an ultrasonic imaging apparatus according to an embodiment of the present invention will be described with reference to FIGS. 1 to 8C, and then, a method of determining a beamforming coefficient and a beamforming method will be described with reference to FIGS. 9 to 13.

(1) An ultrasonic imaging apparatus according to an embodiment of the present invention will be described with reference to FIGS. 1 to 8C.

Figure 1:
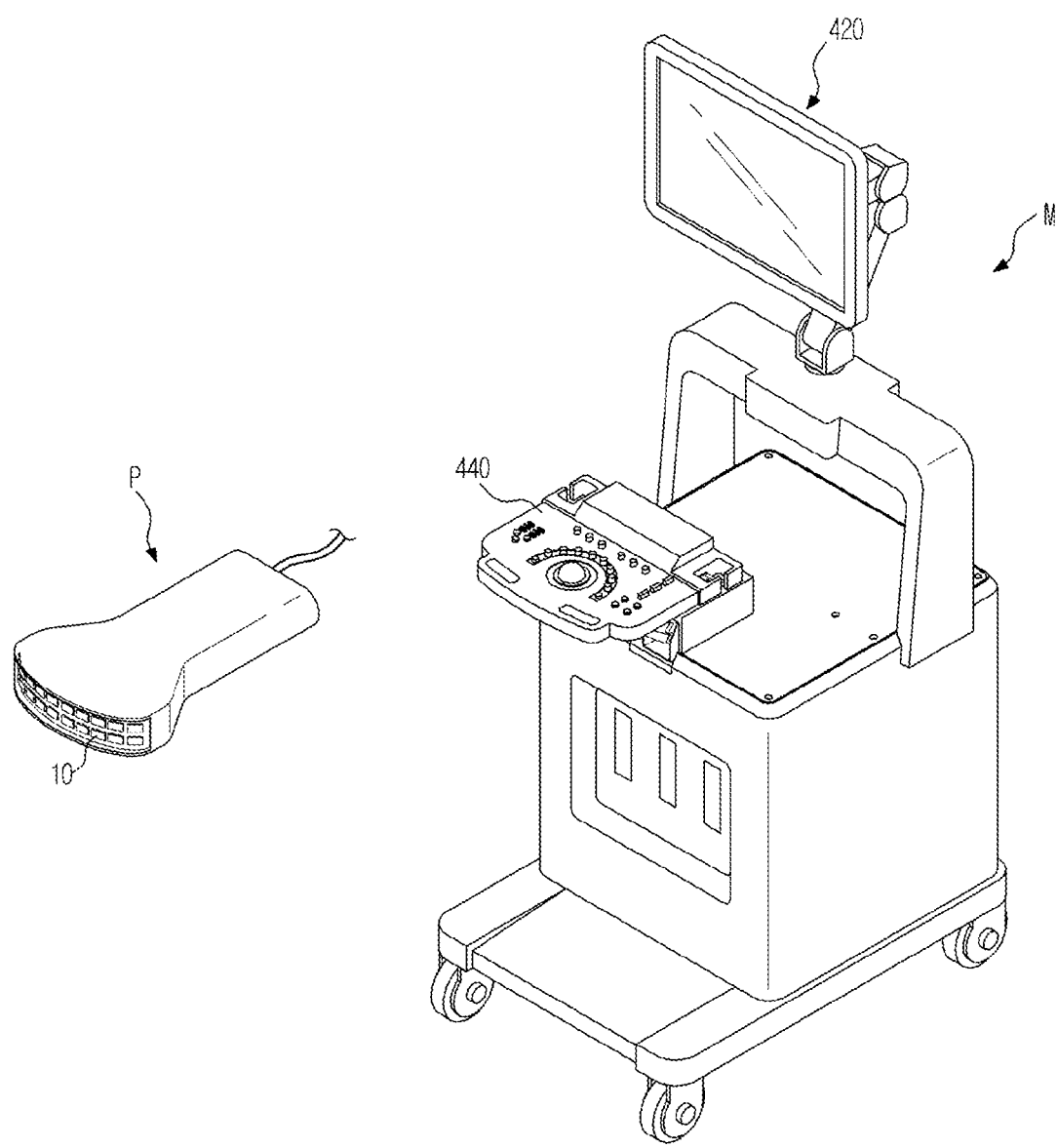
FIG. 1 is a diagram of an ultrasonic imaging apparatus according to an embodiment of the present invention.
Figure 2:
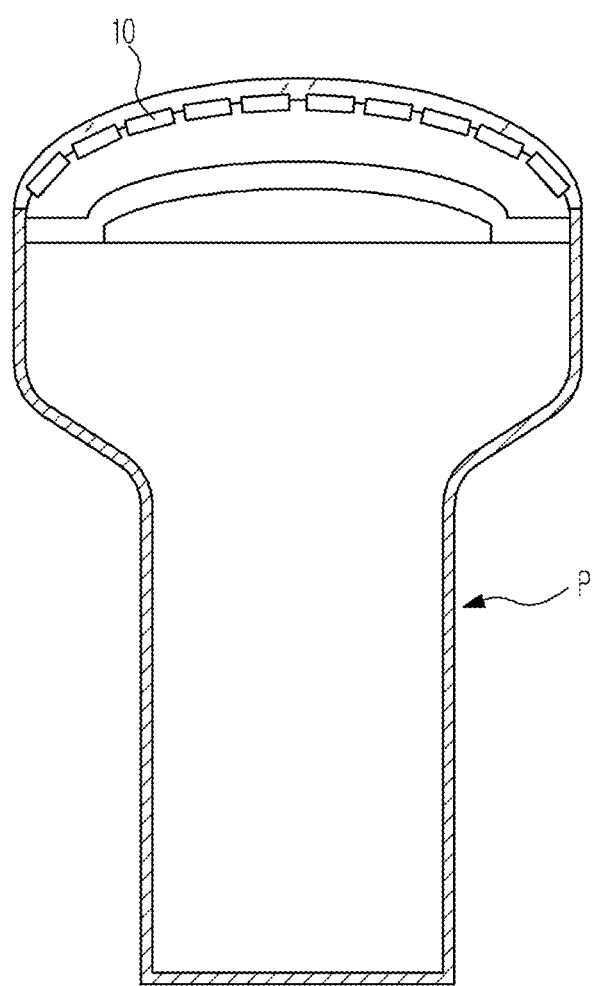
FIG. 2 is a diagram of an ultrasonic probe shown in FIG. 1.

FIG. 1 is a diagram of an ultrasonic imaging apparatus according to an embodiment of the present invention and FIG. 2 is a diagram of an ultrasonic probe P shown in FIG. 1.

As shown in FIG. 1, according to the present embodiment, the ultrasonic imaging apparatus includes the ultrasonic probe P and a main body M.

As seen from FIGS. 1 and 2, the ultrasonic probe P may include a plurality of ultrasonic transducers 10 formed at an end portion thereof, which generate ultrasonic waves according to an electrical signal.

An ultrasonic transducer 10 is a device for generation of ultrasonic waves according to supplied alternating current (AC) power. In detail, the ultrasonic transducers 10 receive AC power from an external power supply or an internal capacitor, for example, a battery or the like, and a piezoelectric or thin film of the ultrasonic transducers 10 vibrates according to the received AC power to generate the ultrasonic waves.

Various ultrasonic transducers may be used as the ultrasonic transducers 10, for example, a magnetostrictive ultrasonic transducer using a magnetostrictive effect, which is mainly used in a conventional ultrasonic probe device, a piezoelectric ultrasonic transducer using a piezoelectric effect of a piezoelectric material, or a capacitive micromachined ultrasonic transducer (cMUT), which transmits and receives ultrasonic waves using vibration of several hundreds or several thousands of micromachined thin films.

The ultrasonic transducers 10 may be fixed to a fixed frame that is disposed on the end portion of the ultrasonic probe P and has a planar shape, a curved shape, or various other shapes and may be arranged to correspond to an external shape of the fixed frame. The fixed frame may be used to fix the ultrasonic transducers 10 and may be formed of a flexible material such as silicon or may be formed of various other materials which are used to fix the ultrasonic transducers 10 in general.

The ultrasonic imaging apparatus radiates the ultrasonic wave generated by the ultrasonic transducers 10 to an external target object, for example, a human body. The radiated ultrasonic waves are reflected by internal materials, that is, targets positioned at various depths of the target object. Then, the ultrasonic transducers 10 receive a reflected ultrasonic echo signal and convert the reflected ultrasonic echo signal into an electrical signal. In addition, the ultrasonic probe P or the main body M may perform predetermined processes on the converted electrical signal to generate an ultrasonic image and may display the ultrasonic image on a display unit 420 that is fixed on the main body M or is connected to the main body M via a wired or wireless network such that a user of the ultrasonic imaging apparatus, for example, a doctor or a nurse, may diagnose the target object, for example, a patient through the ultrasonic image.

Figure 3A:
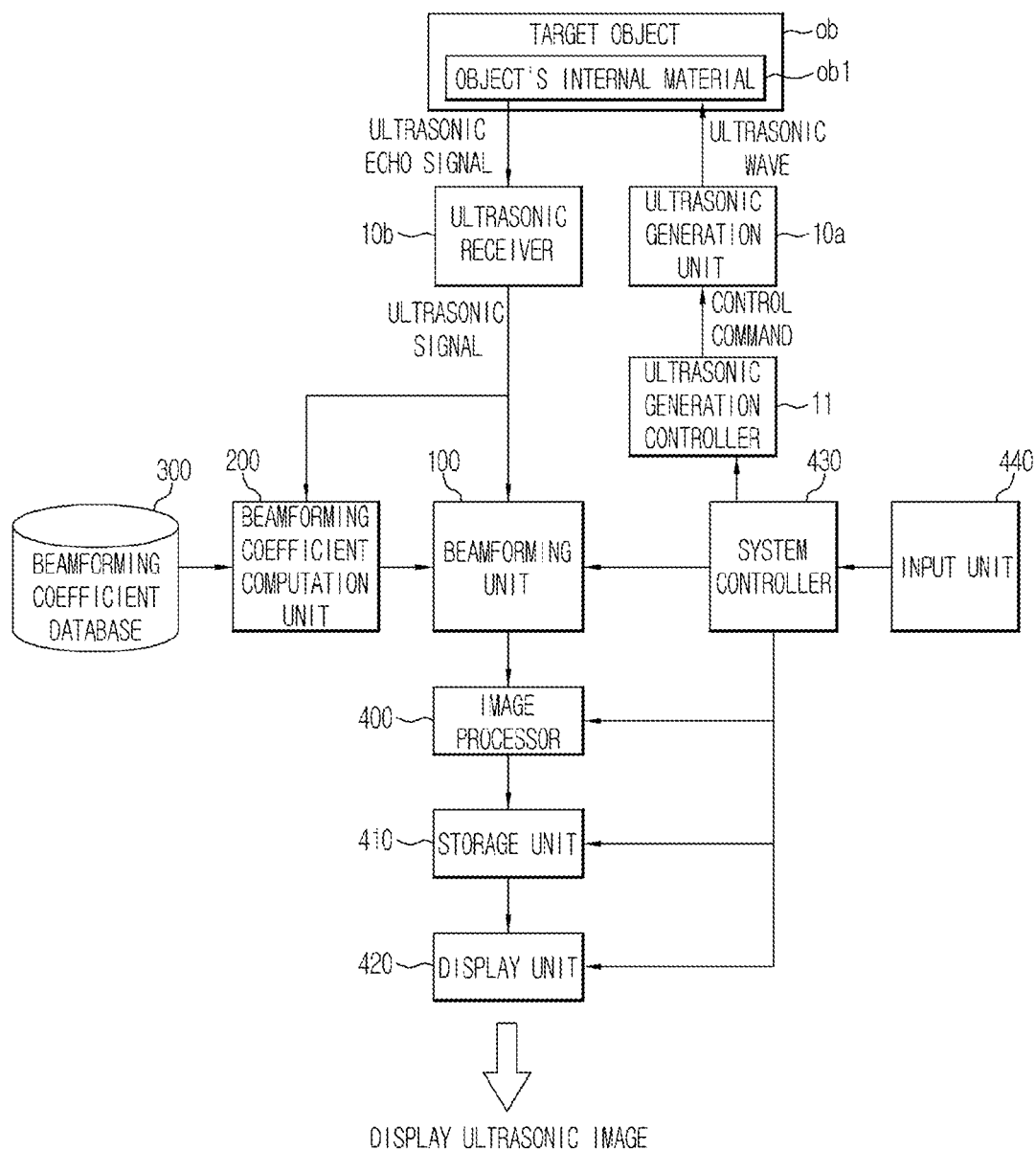
FIG. 3A is a diagram of an overall structure of an ultrasonic imaging apparatus according to an embodiment of the present invention.

Hereinafter, an ultrasonic imaging apparatus according to an embodiment of the present invention will be described in detail with reference to FIG. 3A. FIG. 3A is a diagram of an overall structure of an ultrasonic imaging apparatus according to an embodiment of the present invention.

The ultrasonic imaging apparatus according to the present embodiment may include an ultrasonic generation unit 10$a$, an ultrasonic receiver 10$b$, a beamforming unit 100, a beamforming coefficient computation unit 200, a beamforming coefficient database 300, and an image processor 400.

From these elements, the ultrasonic generation unit 10$a$ and the ultrasonic receiver 10$b$ may be formed in the ultrasonic probe P.

According to embodiments of the present invention, the beamforming unit 100, the beamforming coefficient computation unit 200, the beamforming coefficient database 300, and the image processor 400 may be formed in the ultrasonic probe P, or alternatively, may be formed in the main body M. Some of the beamforming unit 100, the beamforming coefficient computation unit 200, the beamforming coefficient database 300, and the image processor 400 may be formed in the ultrasonic probe P and other remaining elements may be formed in the main body M.

The ultrasonic generation unit 10$a$ generates ultrasonic waves and radiates a target object ob with the ultrasonic waves according to a control command of an ultrasonic generation controller 11.

The ultrasonic receiver 10$b$ receives, as an input, an ultrasonic echo signal reflected from an object's internal material ob1 of the target object ob, that is, a target and converts the ultrasonic echo signal (hereinafter, referred to as an ultrasonic signal) into an electrical signal to output the ultrasonic signal. The output ultrasonic signal is transmitted to the beamforming unit 100 and/or the beamforming coefficient computation unit 200.

According to the ultrasonic imaging apparatus according to an embodiment of the present invention, as described above, the ultrasonic generation unit 10$a$ and the ultrasonic receiver 10$b$ may correspond to the transducer 10 installed in the ultrasonic probe P, and an individual transducer 10 may function as both the ultrasonic generation unit 10a and the ultrasonic receiver 10b.

The ultrasonic signal converted by the ultrasonic receiver 10b, for example, the ultrasonic transducer 10 is transmitted to the beamforming unit 100.

The beamforming unit 100 focuses a plurality of ultrasonic signals output from a plurality of ultrasonic receivers 10b, for example, the ultrasonic transducers 10 to output an ultrasonic focusing signal. The output ultrasonic focusing signal is transmitted to the image processor 400.

According to an embodiment of the present invention, the beamforming unit 100 may compensate for a time difference of ultrasonic signals of ultrasonic channels output from the respective ultrasonic transducers 10, apply predetermined weights, that is, beamforming coefficients to the respective ultrasonic channels so as to emphasize a signal at a predetermined position and to relatively attenuate a signal at another predetermined position, and focus ultrasonic signals.

According to an embodiment of the present invention, the ultrasonic imaging apparatus may include the beamforming coefficient computation unit 200.

The beamforming coefficient computation unit 200 selects some of a plurality of ultrasonic signals received by the ultrasonic receiver 10b and determines optimal beamforming coefficients for the selected ultrasonic signals to determine a beamforming coefficient candidate group. In addition, the beamforming coefficient computation unit 200 selects at least one final beamforming coefficient for optimization of a beamforming computation result of all received ultrasonic signals, from the plurality of beamforming coefficients of the beamforming coefficient candidate group so as to calculate beamforming coefficients that are applied to respective channels for beamforming by the beamforming unit 100.

According to an embodiment of the present invention, the beamforming coefficient computation unit 200 of the ultrasonic imaging apparatus may read the beamforming coefficient database 300 which will be described below to determine the beamforming coefficient candidate group.

In this case, the beamforming coefficient computation unit 200 reads the beamforming coefficient database 300 and extracts some of the beamforming coefficients stored in the beamforming coefficient database 300 to determine the beamforming coefficient candidate group. Here, the beamforming coefficients extracted by the beamforming coefficient computation unit 200 may be selected based on a beamforming computation result of the ultrasonic signals that are selected from the plurality of ultrasonic signals by the beamforming coefficient computation unit 200 according to pre-stored settings or user input.

Figure 3B:
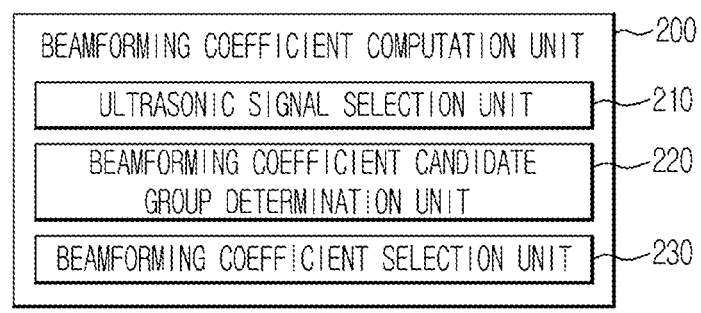
FIG. 3B is a block diagram of a beamforming coefficient computation unit according to an embodiment of the present invention.

FIG. 3B is a block diagram of the beamforming coefficient computation unit 200 according to an embodiment of the present invention.

In detail, as shown in FIG. 3B, the beamforming coefficient computation unit 200 may include an ultrasonic signal selection unit 210, a beamforming coefficient candidate group determination unit 220, and a beamforming coefficient selection unit 230.

Here, the ultrasonic signal selection unit 210 selects some of a plurality of input ultrasonic signals and transmits the selected ultrasonic signals to the beamforming coefficient candidate group determination unit 220.

The beamforming coefficient candidate group determination unit 220 selects a beamforming coefficient candidate group based on a beamforming computation result of the ultrasonic signals selected from the plurality of ultrasonic signals.

For example, the beamforming coefficient candidate group determination unit 220 searches for a beamforming coefficient appropriate for beamforming of the selected ultrasonic signals, among the beamforming coefficients of the beamforming coefficient database 300 which will be described below. In this case, the beamforming coefficient candidate group determination unit 220 may detect one optimal beamforming coefficient, or alternatively, may detect an appropriate number of beamforming coefficients for beamforming of the selected ultrasonic signals. In this case, the number of the detected beamforming coefficients may be set in advance or may be changed according to user manipulation.

The beamforming coefficient selection unit 230 may select at least one beamforming coefficient from the beamforming coefficient candidate group generated by the beamforming coefficient candidate group determination unit 220. In this case, the selected beamforming coefficient may be optimal to beamforming of a plurality of ultrasonic signals or some of a plurality of ultrasonic signals.

The beamforming coefficient candidate group determination unit 220 may select the optimal beamforming coefficients using the ultrasonic signals selected from the received ultrasonic signals to make one or more beamforming coefficient candidate group and the beamforming coefficient selection unit 230 may select the beamforming coefficient using all of the received ultrasonic signals or the ultrasonic signals selected from the received ultrasonic signals, for example, some of the received ultrasonic signals, which are not used by the beamforming coefficient candidate group determination unit 220.

In addition, according to the present embodiment, the ultrasonic imaging apparatus may include the beamforming coefficient database 300 constructed using a plurality of beamforming coefficients.

The beamforming coefficient database 300 may be constructed using various beamforming coefficients for ultrasonic beamforming, for example, beamforming coefficients for optimization of an ultrasonic beamforming computation result.

The beamforming coefficient database 300 may be constructed using beamforming coefficients acquired based on actual tissue data extracted from the target object ob or the object's internal material ob1, for example, a human body. In this case, for example, a plurality of beamforming coefficients may be calculated based on the actual tissue data of the target object ob and the object's internal material ob1 using another computing apparatus, and then, the beamforming coefficient database 300 may be constructed using the computation result.

According to embodiments of the present invention, the beamforming coefficient database 300 may store, as a representative value, beamforming coefficients that are generally and often used among the plurality of beamforming coefficients for optimization of the beamforming computation result, which are acquired based on the various actual tissue data as described above.

Figure 4A:
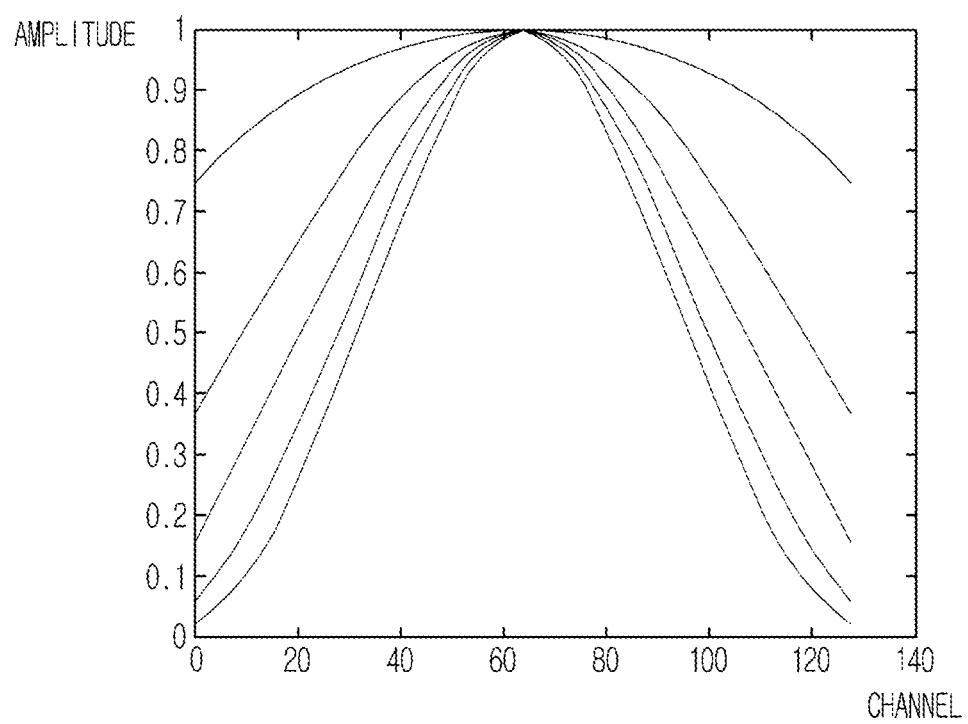
FIGS. 4A and 4B are diagrams for explaining examples of a beamforming coefficient database.
Figure 4B:
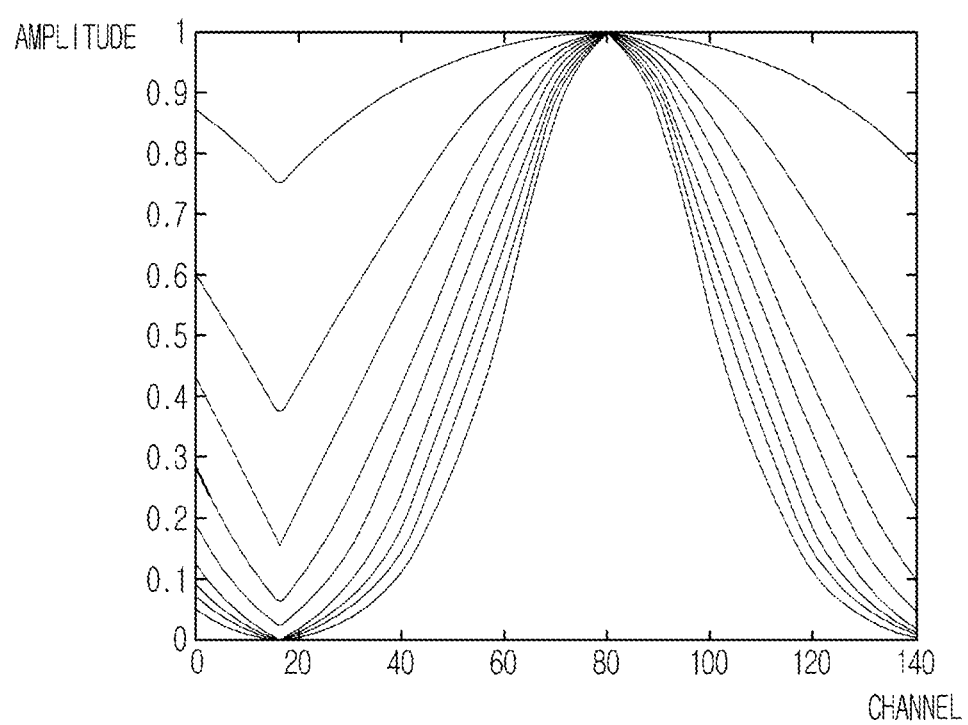

FIGS. 4A and 4B are diagrams for explaining examples of the beamforming coefficient database 400.

Beamforming coefficients may be generated as windows with various shapes formed by changing an amplitude or phase of a signal in a predetermined period, as shown in FIGS. 4A and 4B. In addition, the windows may be rotated or values obtained by inverting the windows, for example, inverse numbers or inverse functions may be calculated to generate windows with various shapes, and the beamforming coefficient database 300 may be constructed using the generated windows.

In addition, it may be possible to construct the beamforming coefficient database 300 using all the windows.

As a design example of the beamforming coefficient database 300, referring to FIG. 4A, beamforming coefficients may be acquired according to windows designed to have various beamwidths and side robe characteristics, and the beamforming coefficient database 300 may be constructed using the beamforming coefficients.

In addition, as shown in FIG. 4B, new windows may be designed by moving a plurality of curves shown in FIG. 4A in a predetermined direction, for example, in a right direction and connecting falling curves of a right side of FIG. 4A to a left side of curves shown in FIG. 4B, and the beamforming coefficient database 300 may be constructed using the new windows.

According to an embodiment of the present invention, the ultrasonic imaging apparatus may include the image processor 400 to generate an image based on beamformed ultrasonic signals. In other words, the image processor 400 may generate an ultrasonic image based on the ultrasonic signals which are received by the ultrasonic receiver 10b, for example, the ultrasonic transducers 10 and are beamformed by the beamforming unit 100, and may transmit the ultrasonic signals to a storage unit 410 or the display unit 420.

According to an embodiment of the present invention, the ultrasonic imaging apparatus may further include the ultrasonic generation controller 11 to generate a control command for generation and radiation of ultrasonic waves and to transmit the control command to the ultrasonic generation unit 10a, as shown in FIG. 3A.

In addition, as shown in FIGS. 1 and 3A, the ultrasonic imaging apparatus may further include the storage unit 410 to store the ultrasonic image generated by the image processor 400, and the display unit 420 to externally output the ultrasonic image stored in the storage unit 410 or output from the image processor 400 such that a user may view the ultrasonic image.

The ultrasonic imaging apparatus may further include a system controller 430 that generates a predetermined control command of an element such as each of the ultrasonic generation controller 11, the beamforming unit 100, the beamforming coefficient computation unit 200, the image processor 400, the storage unit 410, and/or the display unit 420 as described above, transmits the control command to each element, and controls each element. In this case, the system controller 430 may receive a predetermined command from a user through an input unit 440 shown in FIGS. 1 and 3A and may generate and transmit the control command for control of each of the aforementioned elements according to the received command.

(2) Hereinafter, the ultrasonic imaging apparatus according to an embodiment of the present invention will be described in more detail.

Figure 5:
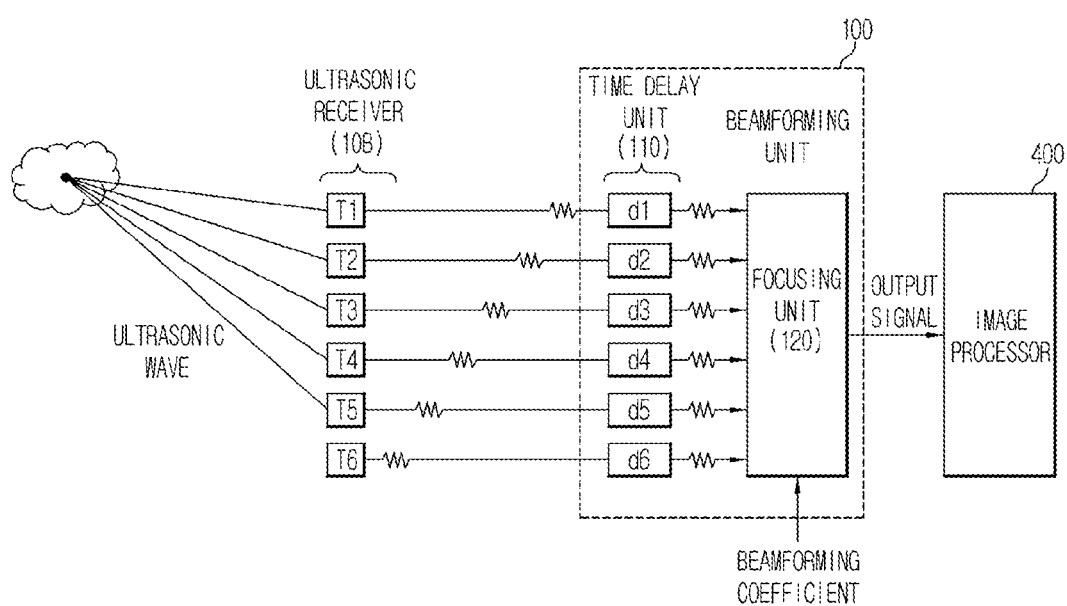
FIG. 5 is a diagram for explaining beamforming according to an embodiment of the present invention.

FIG. 5 is a diagram for explaining beamforming of an ultrasonic imaging apparatus according to an embodiment of the present invention.

As shown in FIG. 5, the ultrasonic imaging apparatus receives a plurality of ultrasonic echo signals reflected from the target object ob or the object's internal material or tissue ob1 through a plurality of ultrasonic receivers 10b, for example, a plurality of transducers 10.

Then, each ultrasonic receiver 10b, for example, T1 through T6 outputs an electrical signal, that is, an ultrasonic signal corresponding to the received ultrasonic echo signal according to the ultrasonic echo signal, and transmits the ultrasonic signal to the beamforming unit 100. In this case, the ultrasonic receiver 10b, for example, T1 through T6 may output ultrasonic signals to a plurality of channels corresponding to the plurality of ultrasonic receivers 10b, for example, T1 through T6.

As shown in FIG. 5, according to an embodiment of the present invention, the beamforming unit 100 may include a time delay unit 110 and a focusing unit 120.

When each ultrasonic receiver 10b, for example, T1 through T6 receives the ultrasonic echo signal, the ultrasonic receivers T1 through T6 may receive ultrasonic waves reflected from the same point at different times because distances between the ultrasonic receivers T1 through T6 and the object's internal material or tissue ob1 from which ultrasonic waves are reflected are different. Thus, the ultrasonic receivers T1 through T6 may also output ultrasonic signals at different times even if the ultrasonic echo signals are received from the same reflection position. That is, a time difference may be present between the ultrasonic signals output from the ultrasonic receivers T1 through T6.

Thus, before the ultrasonic signals output from the ultrasonic receivers T1 through T6 are focused, the time difference in the ultrasonic signals needs to be corrected.

The time delay unit 110 may correct the time difference (a channel delay value) in the ultrasonic signals output from the ultrasonic receivers 10b to focus ultrasonic echo signals reflected from the same position, that is, the target object ob or the object's internal material or tissue ob1.

According to an embodiment of the present invention, the time delay unit 110 may delay the ultrasonic signals output from the ultrasonic receivers 10b by corresponding periods of time to output ultrasonic signals shown in FIG. 5 formed by correcting the time difference of the ultrasonic signals of the ultrasonic receivers T1 through T6.

The ultrasonic signals, a time difference of which is corrected by the time delay unit 110, are transmitted to the focusing unit 120.

The focusing unit 120 may focus the transmitted ultrasonic signals at a predetermined position so as to perform beamforming.

The focusing unit 120 may apply predetermined weights to the respective ultrasonic signals to emphasize specific ultrasonic signals collected by several specific ultrasonic receivers 10b and to relatively attenuate ultrasonic signals collected by other ultrasonic receivers 10b and add the result values in order to beamform a plurality of ultrasonic signals.

According to an embodiment of the present invention, the focusing unit 120 may read predetermined weights, in detail, beamforming coefficients required to focus ultrasonic waves from a database stored in a separate storage medium and may apply the weights to respective ultrasonic signals in order to perform beamforming.

In this case, the beamforming coefficients may be generated as windows with various shapes formed by changing an amplitude or phase of a signal in a predetermined period, as shown in FIGS. 4A and 4B.

According to an embodiment of the present invention, the focusing unit 120 may perform beamforming using the beamforming coefficients according to the following expressions.

The focusing unit 120 focuses the plurality of ultrasonic signals, the time difference of which is corrected, to output a focusing signal and transmits the focusing signal to the image processor 400. The image processor 400 may generate an ultrasonic image based on the focusing signal and may display the ultrasonic image on the display unit 420.

Figure 6:
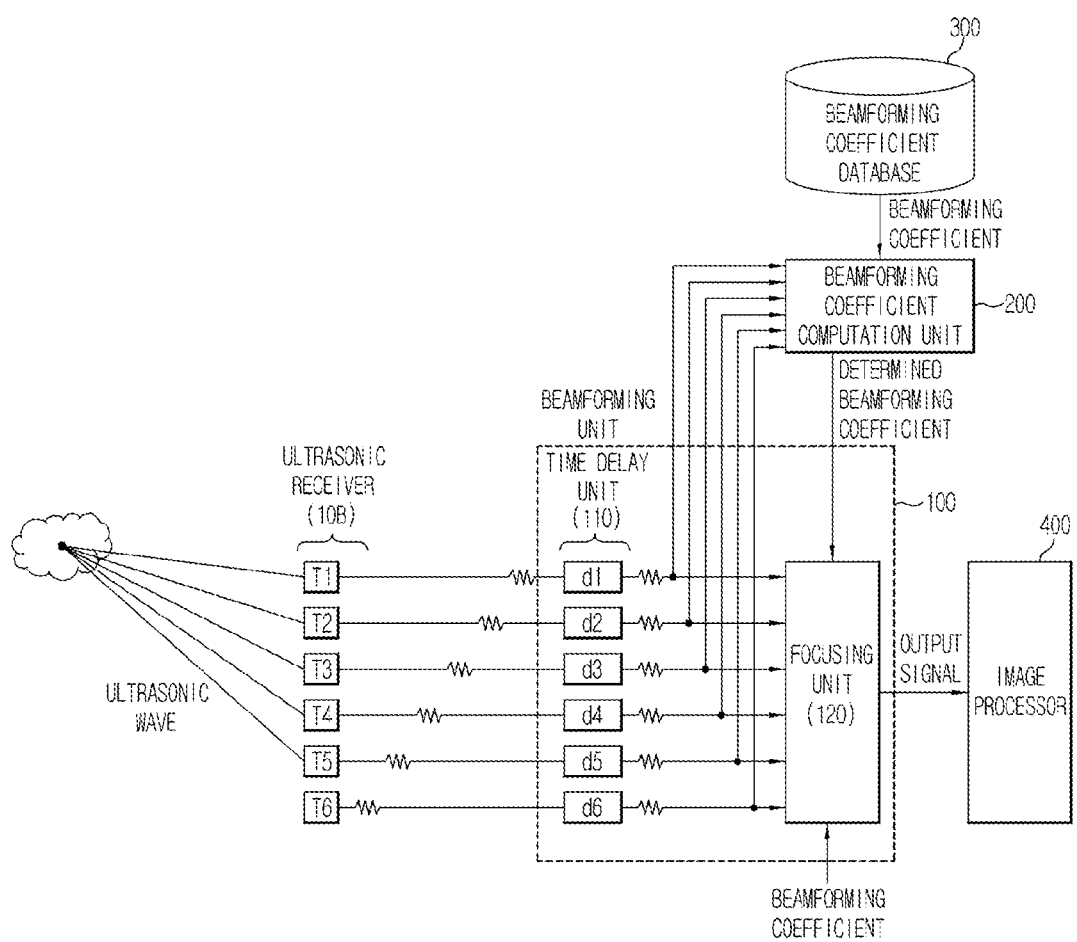
FIG. 6 is a diagram for explaining beamforming performed by a beamforming coefficient computation unit and a beamforming unit, according to an embodiment of the present invention.

FIG. 6 is a diagram for explaining beamforming performed by the beamforming coefficient computation unit 200 and the beamforming unit 100, according to an embodiment of the present invention.

As shown in FIG. 6, an ultrasonic imaging apparatus according to an embodiment of the present invention may include the beamforming coefficient computation unit 200 and may further include the beamforming coefficient database 300.

The beamforming coefficient computation unit 200 receives the plurality of ultrasonic signals, the time difference of which is corrected by the time delay unit 110, separately from the focusing unit 120, reads the beamforming coefficient database 300 to determine at least one beamforming coefficient, and transmits the determined beamforming coefficient to the focusing unit 120. Then, the focusing unit 120 may perform beamforming based on the transmitted beamforming coefficient.

Figure 7:
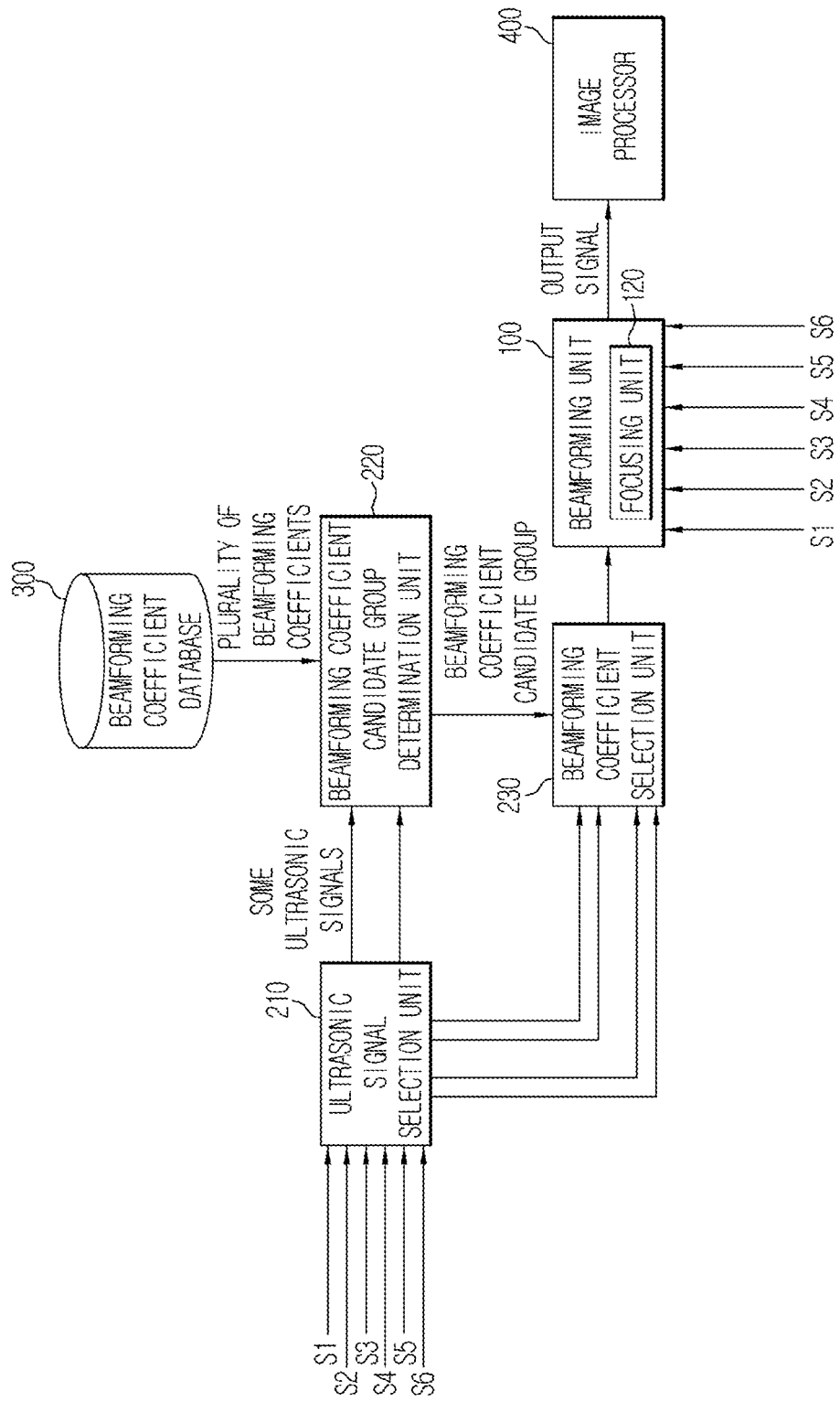
FIG. 7 is another diagram for explaining beamforming performed by a beamforming coefficient computation unit and a beamforming unit, according to an embodiment of the present invention.

FIG. 7 is another diagram for explaining beamforming performed by the beamforming coefficient computation unit 200 and the beamforming unit 100, according to an embodiment of the present invention.

In more detail, the beamforming coefficient computation unit 200 may include the ultrasonic signal selection unit 210, the beamforming coefficient candidate group determination unit 220, and the beamforming coefficient selection unit 230, as shown in FIG. 7.

The ultrasonic signal selection unit 210 may receive the plurality of ultrasonic signals, the time difference of which is corrected by the time delay unit 110 and may select some of the transmitted ultrasonic signals among the plurality of received ultrasonic signals according to a predetermined standard. The selected ultrasonic signals are transmitted to the beamforming coefficient candidate group determination unit 220.

Figure 8B:
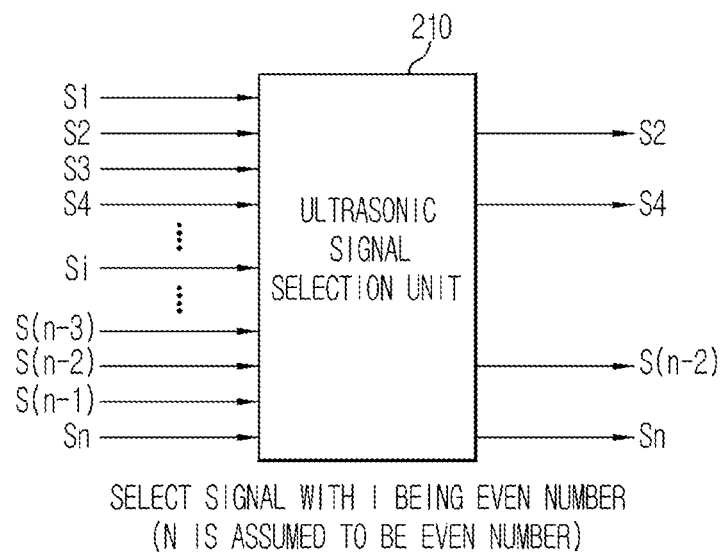
Figure 8C:
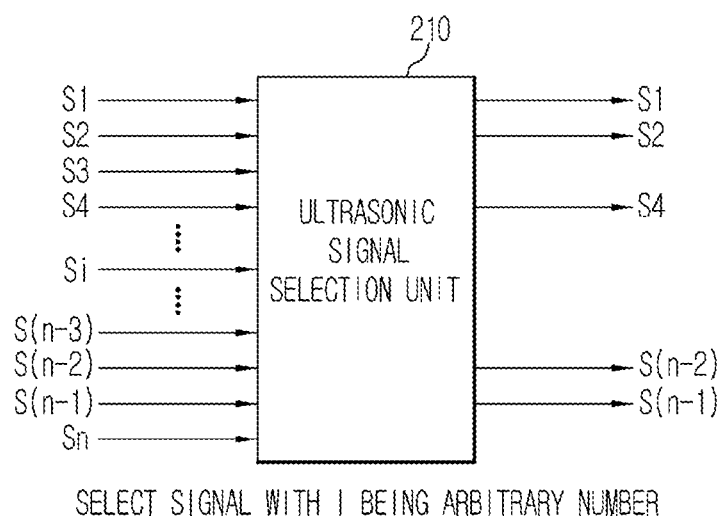

FIGS. 8A through 8C are diagrams for explaining selection of ultrasonic waves by the ultrasonic signal selection unit 210, according to embodiments of the present invention.

According to an embodiment of the present invention, as shown in FIGS. 8A through 8C, the ultrasonic signal selection unit 210 may select only ultrasonic signals, each channel index i of which corresponds to a predetermined condition, from a plurality of ultrasonic signals si ($1 \leq i \leq n$ where n is a natural number) and may transmit the selected ultrasonic signal to the beamforming coefficient candidate group determination unit 220. In this case, a channel index i is an index assigned to each channel of a plurality of ultrasonic signals in order to distinguish between a plurality of channels.

For example, as shown in FIG. 8A, the ultrasonic signal selection unit 210 may select only ultrasonic signals, each channel index i of which is an odd number, from the plurality of input ultrasonic signals $s_i$ and may transmit the selected ultrasonic signals to the beamforming coefficient candidate group determination unit 220. In other words, as shown in FIG. 8A, when n is assumed to be an even number, ultrasonic signals $s_1, s_3, s_5 \ldots s_{(n-1)}$, each channel index i is an odd number, may be selected from a plurality of input ultrasonic signals $s_1$ through $s_n$ and may be output.

As another example, as shown in FIG. 8B, the ultrasonic signal selection unit 210 may select only ultrasonic signals, each channel index i of which is an even number, from the plurality of input ultrasonic signals $s_i$ and may transmit the selected ultrasonic signals to the beamforming coefficient candidate group determination unit 220. That is, as shown in FIG. 8B, when n is assumed to be an even number, ultrasonic signals $s_2, s_4, \ldots s_{(n-2)}$, and $s_n$ may be selected from the plurality of ultrasonic signals $s_1$ through $s_n$ and may be transmitted to the beamforming coefficient candidate group determination unit 220.

As another example, as shown in FIG. 8C, the ultrasonic signal selection unit 210 may arbitrarily select several ultrasonic signal from the plurality of input ultrasonic signals $s_i$. That is, some ultrasonic signals may be arbitrarily selected from the plurality of ultrasonic signal $s_1$ through $s_n$ regardless of a channel index i to output, for example, ultrasonic signals $s_1, s_2, S_4, \ldots s_{(n-2)}$, and $s_{1n-1}$).

As various other methods, for example, the ultrasonic signal selection unit 210 may select some of the plurality of input ultrasonic signals by selecting ultrasonic signals, each channel index of which is a prime number, or ultrasonic signals, each channel index of which is a multiple of 3.

According to another exemplary embodiment each ultrasonic channel may be associated an integer number between 1 and M of a set "A" defined as A=$\{1, 2, 3, \ldots, M\}$ where M is the total number of channels. Another way of defining the set A is as follows A=$\{n: n$ is integer and $1 \leq n \leq M\}$ (which means the set A including all elements "n" that have the properties listed after the ":"). The set A may include a first sub-set A1 and a second sub-set A2 such that A1∪A2=A (i.e. A1 union with A2 is equal to A) and A1∩A2=∅ (i.e. A1 and A2 do not have common elements).

The sub-set A1 may be defined to include all elements of A which are odd numbers (i.e. A1=$\{1, 3, 5, \ldots\}$ or A1=$\{n: n$ is an odd integer and $1 \leq n \leq M\}$) and the sub-set A2, consequently, includes all elements of A which are even numbers (i.e. A2=$\{2, 4, 6, \ldots\}$ A2=$\{n: n$ is an even integer and $1 \leq n \leq M\}$). The sub-sets A1 and A2 are not limited to the sub-sets described above or to any particular sub-sets. The sub-sets may be defined is various ways as needed. For example, the sub-set A1 may be defined to include all integer numbers between 1 and M which are a multiples of 3 (i.e. 3, 6, 9 . . . ) and consequently the sub-set A2 is defined to include all integer numbers between 1 and M which are not multiples of 3.

Information regarding ultrasonic signals, which are not selected by the ultrasonic signal selection unit 210, may be separately stored. According to embodiments of the present invention, by virtue of a method of determining a beamforming coefficient, a beamforming method, and an ultrasonic imaging apparatus, information regarding the ultrasonic signals, which are not selected by the ultrasonic signal selection unit 210, may be used to select beamforming coefficients by the beamforming coefficient selection unit 230 or to calculate a beamforming computation result, which will be described later.

Hereinafter, among channel indexes to distinguish between ultrasonic signal channels, a channel index of a channel that is selected by the ultrasonic signal selection unit 210 is referred to as a first channel index (that may be expressed by stating that the channel index belongs to a sub-set A1 of the set A) and a channel index of a channel that is not selected is referred to as a second channel index (that may be expressed by stating that the channel index belongs to the sub-set A2 of the set A). Where A=$\{1, 2, 3, \ldots M\}$, M being the total number of ultrasonic channels, and A1 and A2 are sub-sets of A such that A1∪A2=A (i.e. A1 union with A2 is equal to A) and A1∩A2=∅ (i.e. A1 and A2 do not have common elements).

As described above, the ultrasonic signals selected from, for example, the plurality of ultrasonic signals $s_1$ through $s_6$ may be transmitted to the beamforming coefficient candidate group determination unit 220, as shown in FIG. 7, and the beamforming coefficient candidate group determination unit 220 may select beamforming coefficients for optimization of beamforming using the selected ultrasonic signals.

As shown in FIG. 7, the beamforming coefficient candidate group determination unit 220 acquires at least one beamforming coefficient using ultrasonic signals selected from a plurality of ultrasonic signals collected by the ultrasonic receiver 10b and then determines a beamforming coefficient candidate group using the at least one beamforming coefficient.

According to an embodiment of the present invention, the beamforming coefficient candidate group determination unit 220 may read the beamforming coefficient database 300 constructed using a plurality of beamforming coefficients that are predetermined to extract a plurality of beamforming coefficients and may determine the beamforming coefficient candidate group from the extracted beamforming coefficients.

The beamforming coefficient candidate group determination unit 220 may acquire beamforming computation results of the respective beamforming coefficients extracted from the beamforming coefficient database 300. In this case, the beamforming computation results refer to beamforming computation results of a plurality of ultrasonic signals selected by the ultrasonic signal selection unit 210. Likewise, the beamforming coefficient candidate group determination unit 220 may acquire a plurality of beamforming computation results of a plurality of ultrasonic signals for respective beamforming coefficients and then determine at least one beamforming coefficient based on the acquired beamforming computation results to determine a beamforming coefficient candidate group including the at least one beamforming coefficient.

According to an embodiment of the present invention, the beamforming coefficient candidate group determination unit 220 may select a beamforming coefficient by which a beamforming computation result has a minimum variance, from the plurality of beamforming computation results acquired using the respective beamforming coefficients.

In addition, the beamforming coefficient candidate group determination unit 220 may select not only a beamforming coefficient for a minimum variance of a beamforming computation result, but also a plurality of beamforming coefficients such as a beamforming coefficient for a second smallest variance, a beamforming coefficient for a third smallest variance, and the like.

In other words, the beamforming coefficient candidate group determination unit 220 may select a plurality of beamforming coefficients for a relatively small variance compared with other beamforming computation results, from the beamforming computation results acquired using the beamforming coefficients, to determine a beamforming coefficient candidate group.

According to an embodiment of the present invention, the beamforming coefficient candidate group determination unit 220 may determine a beamforming coefficient candidate group according to Expression 1 below.

$$\{w_c\} = \underset{N\text{-best } w_p}{\operatorname{argmin}} \left| \sum_{i \in A} w_p[i] x_n[i] \right| \quad \text{[Expression 1]}$$

In Expression 1 above, $W_c$ is a beamforming coefficient included in a beamforming coefficient candidate group, $W_p[i]$ is a beamforming coefficient extracted from the beamforming coefficient database 300, p is a beamforming coefficient index, i is a first channel index (that may be expressed by i∈A1, which means "i" belongs to the sub-set A1), M is the number of reception ultrasonic channels, and N is the number of beamforming coefficients to be included in the beamforming coefficient candidate group. Here, M and N are each a natural number that is equal to or greater than 1. The summation over i∈A1 means that the expression inside the sum is evaluated for each of the "i" elements of the sub-set A1, then the results are summed.

The function "arg min" (modified by "N-best $w_p$") used above is defined to return a set of N beamforming coefficients {Wc} out of all the acquired beamforming coefficeints {Wp}. The N returned beamforming coefficients {Wc} includes beamforming coefficients starting from the smallest beamforming coefficient {Wp} to an Nth smallest beamforming coefficient of all the acquired beamforming coefficients. The beamforming result corresponding to a beamforming coefficient Wp may be defined, according to Expression 1 above, as:

$$\left| \sum_{i \in A1} Wp[i] Xn[i] \right|$$

As seen above the beamforming coefficient Wp[i] is indexed by the index "i" and therefore includes a series of coefficients associated to each of the indexes "i". For example, if the sub-set of selected channels A1 includes the odd integer numbers between 1 and M (i.e. A1={1, 3, 5, . . . }) then the beamforming coefficient may include a corresponding series of coefficients such as Wp={Wp[1]; W[3]; Wp[5] . . . }. Each of the coefficients Wp[i], in the series forming the Wp beam forming coefficient, may be a real number. Similarly, the beamforming coefficient Wc includes a series of coefficients associated to the "1" index where i∈A1.

Here, the beamforming coefficient index p is an index to distinguish between a plurality of beamforming coefficients acquired from the beamforming coefficient database 300.

As described above, a channel index is an index to distinguish between ultrasonic signal channels of a plurality of ultrasonic signals received through the ultrasonic receiver 10b and the first channel index is an index of an ultrasonic signal channel that is selected by the ultrasonic signal selection unit 210 (that may be expressed by "i∈A1", which means "i" belongs to the sub-set A1).

As described above, the first channel index i may include odd numbers or even numbers, or may be arbitrarily selected. In other words, the first channel index i may be an odd number between 1 and M, an even number between 1 and M, or an arbitrary number between 1 or 2 and M. The channel index i is selected by the ultrasonic signal selection unit 210.

As seen from Expression 1 above, the beamforming coefficient $W_p[i]$ acquired by the beamforming coefficient database 300 is used as a weight of a plurality of ultrasonic signals $x_n[i]$. Each of the ultrasonic signals $x_n[i]$ may be expressed by a real/complex number that may represent an integral of the signal (e.g. voltage vs. time; current vs. time) over a time period. As shown in Expression 1, each ultrasonic signal $x_n[i]$ of a plurality of channels selected by the ultrasonic signal selection unit 210 is multiplied by beamforming coefficients $W_p[i]$ corresponding to the corresponding ultrasonic signals $x_n[i]$, and then, the results of multiplication between the beamforming coefficient $W_p[i]$ and an ultrasonic signal $x_n[i]$ are added to all ultrasonic channels. This way beamforming computation results may be acquired.

With respect to all beamforming coefficients $W_p[i]$ extracted by the beamforming coefficient database 300, a plurality of beamforming computation results may be acquired by applying the beamforming coefficients $W_p[i]$ to Expression 1 above. Thus, each beamforming coefficient Wp may be associated a corresponding beamforming computation result.

Then, a beamforming coefficient by which the acquired beamforming computation results are within a predetermined range may be selected from a plurality of beamforming coefficients.

The selected beamforming coefficient may be a beamforming coefficient for minimization of a beamforming computation result among a plurality of beamforming computation results. The function "arg min" in Expression-1 above may perform the aforementioned minimization.

In addition, N beamforming coefficients corresponding to the smallest beamforming computation result to the $N_{th}$ smallest beamforming computation result may be extracted from among the plurality of acquired beamforming coefficients and may be selected to be included in the beamforming coefficient candidate group.

The beamforming coefficient candidate group determination unit 220 may determine a beamforming coefficient candidate group based on at least one beamforming coefficient that is acquired via such computation.

According to another embodiment of the present invention, the beamforming coefficient candidate group determination unit 220 may determine a beamforming coefficient candidate group according to Expression 2 below.

$$\{w_c\} = \underset{w_p}{\text{argmin}} \sum_{k=-K_{coarse}}^{k=K_{coarse}} \left| \sum_{i \in A1} w_p[i] x_{n+k}[i] \right| \quad \text{[Expression 2]}$$

In Expression 2 above, $W_c$ is a beamforming coefficient included in a beamforming coefficient candidate group, $W_p[i]$ is a beamforming coefficient, $x_{n+k}[i]$ is an ultrasonic signal, p is a beamforming coefficient index, i is a first channel index, M is the number of reception ultrasonic channels, N is the number of beamforming coefficients included in the beamforming coefficient candidate group, k is an axial smoothing variable, and $K_{coarse}$ is an upper or lower limit of the smoothing variable for acquisition of a plurality of beamforming coefficients for optimization of beamforming computation results of ultrasonic signals selected from a plurality of input ultrasonic signals.

According to an embodiment of the present invention, a beamforming computation result used to determine a beamforming coefficient may be a beamforming computation result obtained by performing axial smoothing on a plurality of ultrasonic signals.

When axial smoothing is performed to obtain a beamforming computation result, Expression 1 above may be rewritten according to Expression 2 above.

According to Expression 2 above, absolute values of multiplications between beamforming coefficients and ultrasonic signals are added, and then, are added from $K_{coarse}$ to $-K_{coarse}$ as k, for axial smoothing.

In this case, $K_{coarse}$ may be less than or equal to $K_{fine}$ that is used by the beamforming coefficient selection unit 230 that will be described below and may be 0 ($0 \leq K_{coarse} \leq K_{fine}$).

According to Expression 2 above, when the beamforming coefficient candidate group determination unit 220 determines a beamforming coefficient candidate group, if axial smoothing coefficients are calculated, only some axial smoothing coefficients among all axial smoothing coefficients may be calculated, and for example, axial smoothing coefficients are calculated from a case in which an axial smoothing coefficient is $-K_{coarse}$ to a case in which an axial smoothing coefficient is $K_{coarse}$.

Thus, when the beamforming coefficient candidate group determination unit 220 determines a beamforming coefficient candidate group during beamforming using axial smoothing, a beamforming coefficient is also calculated within only a partial range to determine the beamforming coefficient candidate group, thereby reducing computational load required to determine a beamforming coefficient candidate group.

According to another embodiment of the present invention, the beamforming coefficient candidate group determination unit 220 may determine a beamforming coefficient candidate group using a beamforming computation result obtained by performing smoothing using adjacent beam data Tx for imaging without using the beamforming computation result obtained by performing axial smoothing as shown in Expression 2 above.

According to an embodiment of the present invention, the beamforming coefficient candidate group determination unit 220 may determine a beamforming coefficient candidate group according to Expression 3 below instead of Expression 1 above.

$$\{w_c\} = \underset{w_p}{\text{argmin}} \left| \sum_{i \in A1} w_p[i] x_n[i] \right|^2 \quad \text{[Expression 3]}$$

According to another embodiment of the present invention, the beamforming coefficient candidate group determination unit 220 may determine a beamforming coefficient candidate group based on the beamforming computation result obtained by performing axial smoothing on a plurality of ultrasonic signals according to Expression 4 below instead of Expression 2 above.

$$\{w_c\} = \underset{w_p}{\text{argmin}} \sum_{k=-K_{coarse}}^{k=K_{coarse}} \left| \sum_{i \in A1} w_p[i] x_{n+k}[i] \right|^2 \quad \text{[Expression 4]}$$

Each variable and symbol of Expression 3 and Expression 4 above are the same as in Expression 1 and Expression 2 above.

As described above, a beamforming computation result $S_c$ of at least one beamforming coefficient $W_c$ acquired according to Expression 1 above may be given according to Expression 5 below $$\{S_c\} = \underset{w_p}{\text{min}} \left| \sum_{i \in A1} w_p[i] x_n[i] \right| \quad \text{[Expression 5]}$$

Each symbol of Expression 5 is the same as in Expression 1 above.

As seen from Expression 5, a left side of Expression 5, $S_c$ refers to a value obtained by minimizing an absolute value of addition of multiplication between the beamforming coefficient $W_c$ acquired according to Expression 1 above and an ultrasonic signal corresponding thereto or relatively small N beamforming computation results compared with other results. The function "min" (modified by "N-best $w_p$") used above is defined to return a set of N beamforming computation results Sc out of all the acquired computation results. The N returned beamforming computation results are the smallest N computation results among all the beamforming computation results.

The beamforming computation result $S_c$ may be automatically obtained during the computation of the beamforming coefficient $W_c$.

According to an embodiment of the present invention, a plurality of beamforming coefficients and a plurality of beamforming computation results may be stored in a separate storage unit, that is, the storage unit 410, or may be temporally stored in a storage space of an ultrasonic imaging apparatus, for example, a random access memory (RAM).

The beamforming computation result $S_c$ of the at least one beamforming coefficient $W_c$ acquired according to Expression 2 through Expression 4 above as well as Expression 1 above may also be given according to Expression 6 through Expression 8 below.

$$\{S_c\} = \min_{\substack{N\text{-best } w_p}} \sum_{k=-K_{coarse}}^{k=K_{coarse}} \left| \sum_{i \in A1} w_p[i] x_{n+k}[i] \right| \quad \text{[Expression 6]}$$

$$\{S_c\} = \min_{\substack{N\text{-best } w_p}} \left| \sum_{i \in A1} w_p[i] x_n[i] \right|^2 \quad \text{[Expression 7]}$$

$$\{S_c\} = \min_{\substack{N\text{-best } w_p}} \sum_{k=-K_{coarse}}^{k=K_{coarse}} \left| \sum_{i \in A1} w_p[i] x_{n+k}[i] \right|^2 \quad \text{[Expression 8]}$$

Each symbol of Expression 6 through Expression 8 is the same as in Expression 2 through Expression 4 above. The beamforming computation result Sc of Expression 6 and Expression 8 above refers to a beamforming computation result obtained by performing axial smoothing.

As described above, when a beamforming coefficient candidate group is determined by the beamforming coefficient candidate group determination unit 220, the beamforming coefficient selection unit 230 may select an optimal beamforming coefficient for beamforming among beamforming coefficient candidate groups, as shown in FIG. 7.

According to an embodiment of the present invention, as shown in FIG. 7, the beamforming coefficient selection unit 230 may acquire beamforming computation results of a plurality of ultrasonic signals received by the ultrasonic receiver 10b using beamforming coefficients of a beamforming coefficient candidate group.

Unlike the aforementioned case in which the beamforming coefficient candidate group determination unit 220 acquires beamforming computation results of a plurality of beamforming coefficients extracted by the beamforming coefficient database 300 using the ultrasonic signals selected by the ultrasonic signal selection unit 210, and determines a beamforming coefficient candidate group from the beamforming coefficient database 300 based on the acquired beamforming computation results, the beamforming coefficient selection unit 230 acquires a beamforming computation result obtained using at least one beamforming coefficient extracted from a beamforming coefficient candidate group using all ultrasonic signals or ultrasonic signals selected therefrom, time differences of which are corrected by the time delay unit 110, and determines at least one beamforming coefficient for beamforming based on the acquired beamforming computation result.

According to an embodiment of the present invention, the beamforming coefficient selection unit 230 may select a beamforming coefficient according to Expression 9 below.

Expression 9 below may be generally used when the beamforming coefficient candidate group determination unit 220 uses Expression 1 above or may also be used when a beamforming coefficient candidate group is selected according to Expression 2 through Expression 4 above.

$$\{w_f\} = \operatorname*{argmin}_{w_c} \left[ S_c(w_c^{(n)}) + \left| \sum_{j \in A2} w_c^{(n)}[j] x_n[j] \right| \right] \quad \text{[Expression 9]}$$

In Expression 9 above, $W_f$ is a final selected beamforming coefficient and $S_c(w^{(n)}_c)$ refers to a beamforming computation result of an $n_{th}$ beamforming coefficient $w^{(n)}_c$ among beamforming coefficients $W_c$ of a beamforming candidate group.

In particular, $S_c(w^{(n)}_c)$ is a result value obtained by inserting $w^{(n)}_c$ into Expression 5 above when the beamforming coefficient candidate group determination unit 220 uses Expression 1 above.

When the index i∈A1 (which means "i" belongs to the sub-set A1) the index j∈A2 (which means that index "j" belongs to the subset A2). A1 and A2 are sub-sets of A={1, 2, 3, . . . M}, M being the total number of ultrasonic channels, such that A1∪A2=A (i.e. A1 union with A2 is equal to A) and A1∩A2=∅ (i.e. A1 and A2 do not have common elements). Here, a second channel index j is a channel index to distinguish between ultrasonic signals like the aforementioned first channel index. In an exemplary embodiment the second channel index j may be an odd number between 1 and M (i.e. A2 is the sub-set of A that includes all odd numbers of A). In another embodiment the second channel index j may be an even number between 2 and M (i.e. A2 is the sub-set of A that includes all odd numbers of A). In yet another exemplary embodiment the second channel index j may be an arbitrary number between 1 and M (i.e. A2 is the sub-set of A that includes an arbitrary or random set of elements of A). The second channel index is a channel index of an ultrasonic channel, which does not correspond to the first channel index i among a plurality of ultrasonic channels of a plurality of ultrasonic signals received by the ultrasonic receiver 10b. That is, the second channel index j refers to a channel index of the remaining ultrasonic signals which are not selected by the ultrasonic signal selection unit 210, as described above. When the index i∈A1 the index j∈A2 (which means that index "j" belongs to the subset A2). A1 and A2 are sub-sets of A={1, 2, 3, . . . M}, M being the total number of ultrasonic channels, such that A1∪A2=A (i.e. A1 union with A2 is equal to A) and A1∩A2=∅ (i.e. A1 and A2 do not have common elements).

Thus, channels of the first channel index i and the second channel index j are not repeatedly used. In other words, a group of first channel indexes i and a group of second channel indexes j are relatively prime. In other words if i∈A1 and j∈A2 then A1∩A2=∅ (i.e. A1 and A2 do not have common elements).

In addition, all the first channel indexes i and the second channel indexes j may be added to constitute channel indexes of all ultrasonic channels. That is, a union of the group of the first channel indexes i and the group of the second channel indexes j may be a group of ultrasonic channels including ultrasonic channels of ultrasonic signals that are transmitted from the ultrasonic receiver 10b or ultrasonic signals, a time difference of which is corrected by the time delay unit 110. In other words if i∈A1 and j∈A2 then A1∪A2=A (i.e. A1 union with A2 is equal to A) where A={1, 2, 3, . . . M}, M being the total number of ultrasonic channels.

For example, when the first channel index is a group of odd numbers such as 1, 3, 5 . . . , the second channel index j may be a group of even numbers such as 2, 4, 6 . . . . On the contrary, when the first channel index i is a group of even numbers, the second channel index j may be a group of odd numbers.

Thus, an expression within an absolute symbol of Expression 9 above, that is, Expression 9A below means that remaining ultrasonic signals, which are not selected by the ultrasonic signal selection unit 210, are multiplied by weights, that is, beamforming coefficients and are added.

$$\left| \sum_{j \in A2} w_c^{(n)}[j] x_n[j] \right|$$ [Expression 9A]

When the beamforming computation result $S_c(w^{(n)}_c)$ is obtained by inserting $w^{(n)}_c$ into Expression 5 above, the beamforming computation result $S_c(w^{(n)}_c)$ is already calculated by the beamforming coefficient candidate group determination unit 220. This is because the beamforming coefficient $w^{(n)}_c$ is an $n_{th}$ beamforming coefficient among beamforming coefficients $W_c$ of a beamforming candidate group.

Referring back to Expression 5 above, it may be seen that the beamforming computation result $S_c(w^{(n)}_c)$ is an absolute value of addition of multiplications between ultrasonic signals corresponding to the first channel indexes i and beamforming coefficients of the ultrasonic signal. Accordingly, Expression 9 above may be rewritten according to Expression 10 below.

$$\{w_f\} = \operatorname*{argmin}_{w_c} \left[ \left| \sum_{i \in A1} w_c^{(n)}[i] x_n[i] \right| + \left| \sum_{j \in A2} w_c^{(n)}[j] x_n[j] \right| \right]$$ [Expression 10]
$$\quad (1) \quad\quad\quad (2)$$

As seen from Expression 10 above, some of all ultrasonic channels M are calculated according to expression (1) of Expression 10 (i.e. the first term of the argmin function) within a front absolute symbol and remaining some ultrasonic channels are calculated according to expression (2) of Expression 10 (i.e. the second term of the argmin function) within a rear absolute symbol. Accordingly, the beamforming coefficient selection unit 230 may acquire beamforming computation results of all ultrasonic channels, in other words, all ultrasonic signals and may select at least one beamforming coefficient based on the acquired beamforming computation results. Of course, the beamforming coefficient selection unit 230 does not have to calculate expression (1) of Expression 10 above. This is because expression (1) of Expression 10 is already calculated by the beamforming coefficient candidate group determination unit 220. Thus, computational load of the beamforming coefficient selection unit 230 may be reduced.

Thus, the beamforming coefficient selection unit 230 may acquire expression (2) of Expression 10 above using at least one beamforming coefficient of a beamforming coefficient candidate group, add the beamforming computation result $S_c(w^{(n)}_c)$ to a computation result to acquire a final beamforming computation result $S_f$, and select a beamforming coefficient $W_f$ for minimization of the final beamforming computation result $S_f$ from beamforming coefficients $W_c$ of the beamforming candidate group.

According to another embodiment of the present invention, the beamforming coefficient selection unit 230 may select a beamforming coefficient according to Expression 11 below. Expression 11 below may be used in general when the beamforming coefficient candidate group determination unit 220 selects a beamforming coefficient candidate group according to Expression 2 above. However, according to embodiments of the present invention, Expression 11 below may be used when a beamforming coefficient candidate group is determined according to Expression 1, Expression 3, or Expression 4 above.

$$\{w_f\} = \operatorname*{argmin}_{w_c} \left[ S_c(w_c^{(n)}) + \sum_{k \notin K_{coarse}} \left| \sum_{j \in A2} w_c^{(n)}[j] x_{n+k}[j] \right| \right]$$ [Expression 11]

Expression 11 above may be used to select a final beamforming coefficient when axial smoothing is applied. Each symbol of Expression 11 above is the same as in Expression 1 through Expression 4 and Expression 9 above.

Expression 11 above may be calculated with respect to only some axial smoothing coefficient when the axial smoothing is performed. For example, as shown in Expression 11 above, absolute values may be added within the range used in Expression 2 above except for an axial smoothing variable k.

According to another embodiment of the present invention, Expression 11 above means that the absolute values may be added when the axial smoothing variable k is from $-K_{fine}$ to $K_{fine}$. In this case, $K_{fine}$ may be equal to or greater than $K_{coarse}$ ($0 \leq K_{coarse} \leq K_{fine}$).

According to another embodiment of the present invention, the beamforming coefficient selection unit 230 may calculate a beamforming coefficient to be used for beamforming using Expression 12 or Expression 13 below.

In general, Expression 12 below may be used when the beamforming coefficient candidate group determination unit 220 uses Expression 3 above, and Expression 13 below may be used when the beamforming coefficient candidate group determination unit 220 uses Expression 4 above. However, as necessary, when other expressions are used, Expression 12 or Expression 13 below may also be used for calculation of a beamforming coefficient.

$$\{w_f\} = \operatorname*{argmin}_{w_c} \left[ S_c(w_c^{(n)}) + \left| \sum_{j \in A2} w_c^{(n)}[j] x_n[j] \right|^2 \right]$$ [Expression 12]

$$\{w_f\} = \operatorname*{argmin}_{w_c} \left[ S_c(w_c^{(n)}) + \sum_{k \notin K_{coarse}} \left| \sum_{j \in A2} w_c^{(n)}[j] x_{n+k}[j] \right|^2 \right]$$ [Expression 13]

Expression 13 above may be used to select a final beamforming coefficient when axial smoothing is applied. Each symbol of Expression 12 and Expression 13 above is the same as in Expression 1 through Expression 4 and Expression 9 above.

When the beamforming coefficient selection unit 230 selects a beamforming coefficient to be used in beamforming by calculating a beamforming coefficient from a beamforming coefficient candidate group according to Expression 9 above, a beamforming computation result acquired by the beamforming coefficient selection unit 230 is given according to Expression 14 below.

$$\{S_f\} = \min_{w_c} \left[ S_c(w_c^{(n)}) + \left| \sum_{j \in A2} w_c^{(n)}[j] x_n[j] \right| \right] \quad \text{[Expression 14]}$$

A beamforming computation result Sf of a left side of Expression 14 above is a result obtained by inserting a beamforming coefficient calculated from a beamforming coefficient candidate group according to Expression 9 above into Expression 14-A below. In other words, the beamforming computation result Sf is a minimum of Expression 14A below, where the variable of the expression is $W_c^{(n)}$.

$$\left[ S_c(w_c^{(n)}) + \left| \sum_{j \in A2} w_c^{(n)}[j] x_n[j] \right| \right] \quad \text{[Expression 14A]}$$

In addition, according to embodiments of the present invention, when the beamforming coefficient selection unit 230 selects a beamforming coefficient according to Expression 11 above, a beamforming computation result is given according to Expression 15 below.

$$\{S_f\} = \min_{w_c} \left[ S_c(w_c^{(n)}) + \sum_{k \notin K_{coarse}} \left| \sum_{j \in A2} w_c^{(n)}[j] x_{n+k}[j] \right| \right] \quad \text{[Expression 15]}$$

According to another embodiment of the present invention, when the beamforming coefficient selection unit 230 selects a beamforming coefficient according to Expression 12 above, a beamforming computation result is given according to Expression 16 below.

$$\{S_f\} = \min_{w_c} \left[ S_c(w_c^{(n)}) + \left| \sum_{j \in A2} w_c^{(n)}[j] x_n[j] \right|^2 \right] \quad \text{[Expression 16]}$$

According to another embodiment of the present invention, when the beamforming coefficient selection unit 230 selects a beamforming coefficient according to Expression 13 above, a beamforming computation result is given according to Expression 17 below.

$$\{S_f\} = \min_{w_c} \left[ S_c(w_c^{(n)}) + \sum_{k \notin K_{coarse}} \left| \sum_{j \in A2} w_c^{(n)}[j] x_{n+k}[j] \right|^2 \right] \quad \text{[Expression 17]}$$

As described above, when the beamforming coefficient $W_f$ is determined by the beamforming coefficient selection unit 230, the beamforming coefficient $W_f$ is transmitted to the focusing unit 120 of the beamforming unit 100. Then, the focusing unit 120 performs beamforming on a plurality of ultrasonic signals using the beamforming coefficient $W_f$ as a weight. The beamformed ultrasonic signals are transmitted to the image processor 400. Then, the image processor 400 may generate an ultrasonic image based on the beamformed ultrasonic signals and then display the ultrasonic image on the display unit 420.

As described above, the beamforming coefficient computation unit 200 may determine a beamforming coefficient based on a plurality of ultrasonic signals that are reflected from a target object and received by the ultrasonic receiver 10b, for example, the ultrasonic transducers 10 and may transmit the beamforming coefficient to the focusing unit 120, and thus, beamforming may be performed on ultrasonic signals of an entire region of the displayed ultrasonic image.

According to another embodiment of the present invention, the beamforming coefficient computation unit 200 may determine a beamforming coefficient of an ultrasonic signal of only a partial region of the displayed ultrasonic image and may transmit the beamforming coefficient to the focusing unit 120. In other words, the ultrasonic signal selection unit 210 of the beamforming coefficient computation unit 200 may select some of a plurality of ultrasonic signals that are reflected by only a partial region of the target object ob and received, from ultrasonic signals reflected from the target object ob. The beamforming coefficient candidate group determination unit 220 may determine a beamforming coefficient candidate group based on the selected ultrasonic signal. The beamforming coefficient selection unit 230 may determine a beamforming coefficient from the determined beamforming coefficient candidate group.

Thus, the beamforming unit 100 may perform beamforming on a plurality of ultrasonic signals that are reflected by only a partial region of the target object ob and received, using the beamforming coefficient determined by the beamforming coefficient computation unit 200, and may perform beamforming on a plurality of ultrasonic signals that are reflected by another region and received, or may perform beamforming using various conventional known beamforming methods.

According to an embodiment of the present invention, when a compounding method or a synthetic aperture method is used, the aforementioned acquired beamforming coefficient may be commonly used with respect to the same position.

(3) Hereinafter, a beamforming method according to an embodiment of the present invention will be described with reference to FIGS. 9 through 13.

Figure 9:
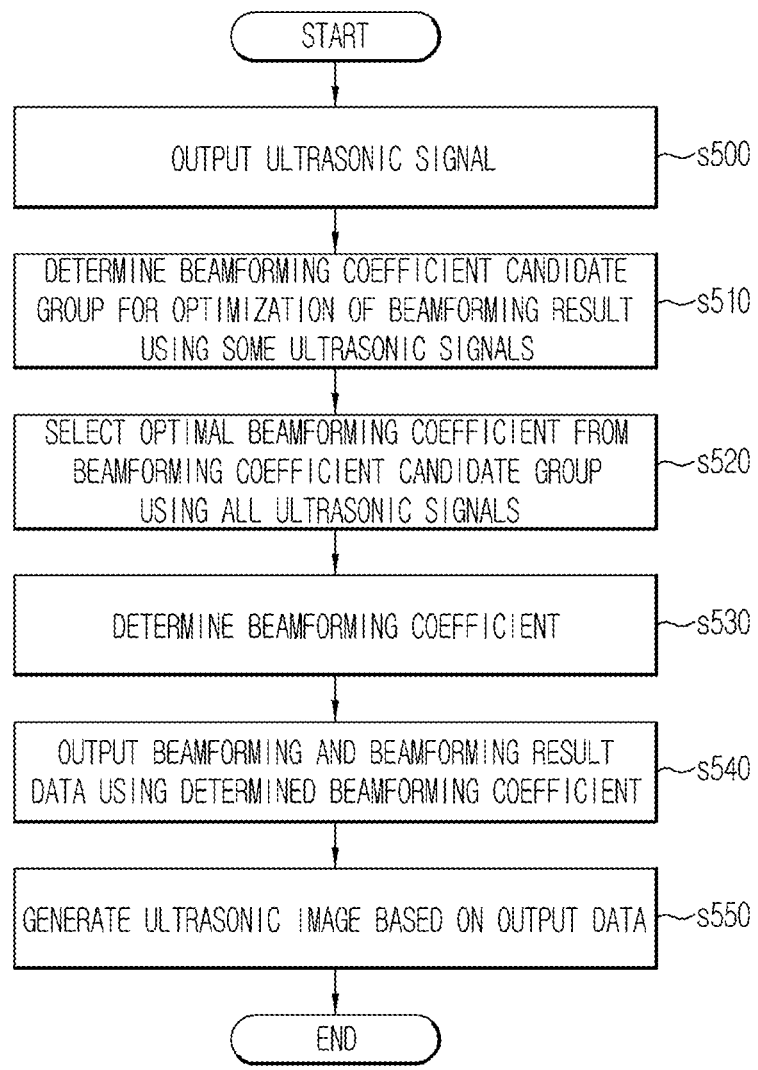
FIG. 9 is a flowchart of a beamforming method according to an embodiment of the present invention.

FIG. 9 is a flowchart of a beamforming method according to an embodiment of the present invention.

As shown in FIG. 9, in the beamforming method according to the present embodiment, first, an ultrasonic signal is output and transmitted to the beamforming coefficient computation unit 200 (s500).

In this case, the ultrasonic signal may be output by the ultrasonic receiver 10b or output by a device to output different other ultrasonic signals.

The beamforming coefficient computation unit 200 may determine a beamforming coefficient candidate group for optimization of a beamforming computation result using some of the output ultrasonic signals (s510).

In this case, according to embodiments of the present invention, the ultrasonic signal used in operation s510 may be selected from the output ultrasonic signals according to a predetermined condition, and for example, may be selected according to whether an ultrasonic channel index is an odd number, an even number, or the like or may be arbitrarily selected.

According to embodiments of the present invention, Expression 1 through Expression 4 above may be used to determine a beamforming coefficient candidate group.

The beamforming coefficient computation unit 200 may determine a beamforming coefficient candidate group using the aforementioned method and may select an optimal beamforming coefficient from the beamforming coefficient candidate group based on the output ultrasonic signal (s520). In beamforming methods according to embodiments of the present invention, in this case, the beamforming coefficient may be selected based on all output ultrasonic signals or may be selected based on some of the output ultrasonic signals.

The selected optimal beamforming coefficient may be determined as a beamforming coefficient to be used in beamforming by the beamforming unit 100 (s530).

The beamforming unit 100 performs beamforming using the beamforming coefficient determined using the aforementioned method to output beamforming result data and transmits the beamforming result data to the image processor 400 (s540). Then, the image processor 400 generates an ultrasonic image based on the beamforming result data output by the beamforming unit 100 (s550).

Hereinafter, a method of determining a beamforming coefficient for beamforming will be described with regard to various embodiments of the present invention.

Figure 10:
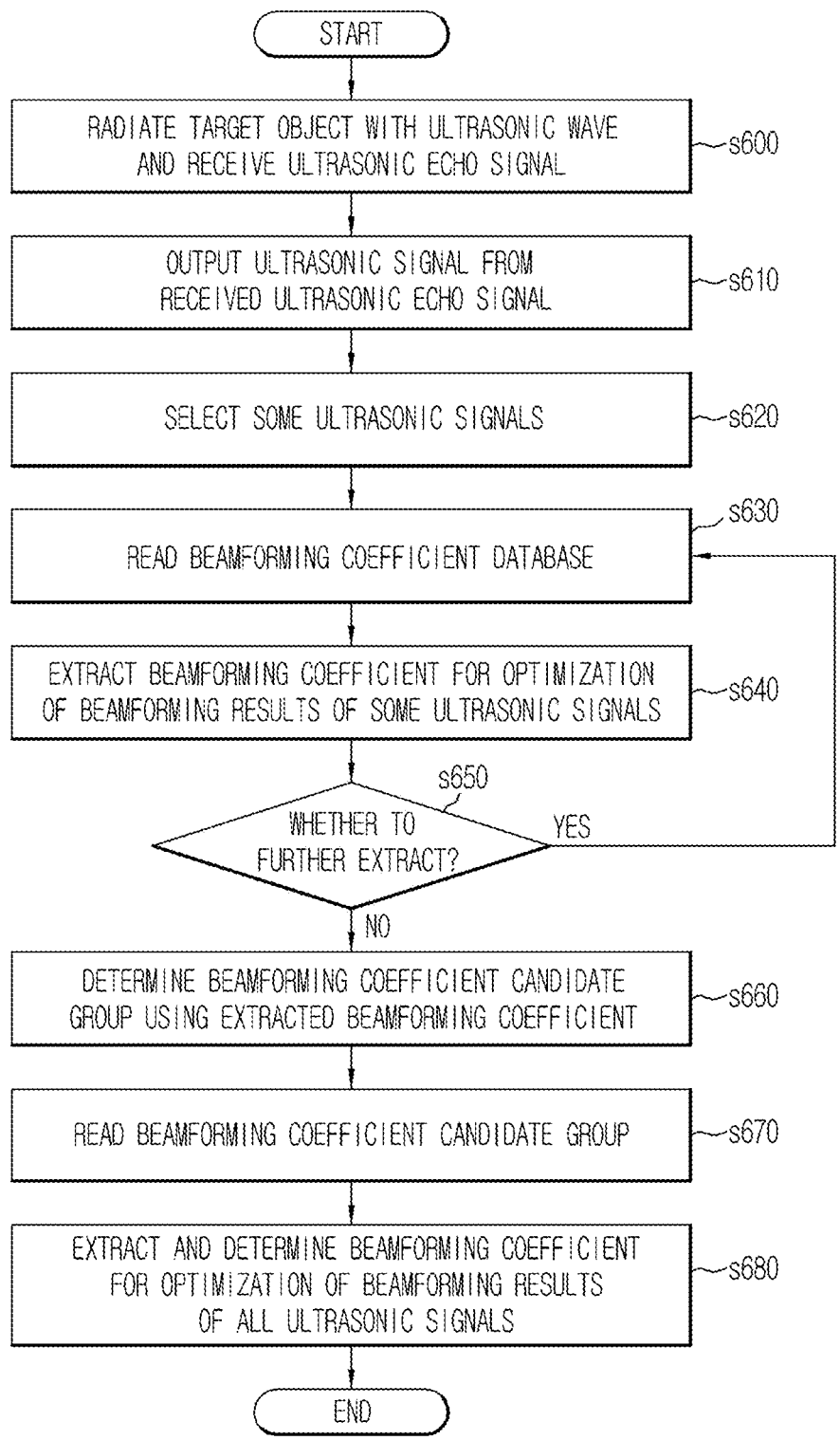
FIG. 10 is a flowchart of a method of determining a beamforming coefficient according to an embodiment of the present invention.

FIG. 10 is a flowchart of a method of determining a beamforming coefficient according to an embodiment of the present invention.

As shown in FIG. 10, in the beamforming coefficient determination method according to the present embodiment, first, the ultrasonic generation unit 10*a* generates ultrasonic waves and radiates a target object with the ultrasonic waves, and the ultrasonic receiver 10*b* receives an ultrasonic echo signal reflected from the target object (s600). The ultrasonic receiver 10*b* outputs an ultrasonic signal from the received ultrasonic echo signal and transmits the ultrasonic signal to the beamforming coefficient computation unit 200 (s610).

The beamforming coefficient computation unit 200 may select some of the output ultrasonic signals (s620), read the beamforming coefficient database 300 (s630), and then, extract a beamforming coefficient for optimization of beamforming computation results of the ultrasonic signals selected from the beamforming coefficient database 300 (s640).

When a beamforming coefficient is further extracted, operations s630 and s640 are repeatedly performed (s650). When a beamforming coefficient is not further extracted, a beamforming coefficient candidate group is determined using the extracted beamforming coefficient (s660).

Then, the beamforming coefficient computation unit 200 may read the beamforming coefficient candidate group determined in the aforementioned operation s660 (s670) and may extract beamforming coefficients for optimization of beamforming results of all or some ultrasonic signals from the read beamforming coefficient candidate group to determine a beamforming coefficient (s680).

Hereafter, a method of determining a beamforming coefficient candidate group will be described with regard to various embodiments of the present invention.

Figure 11:
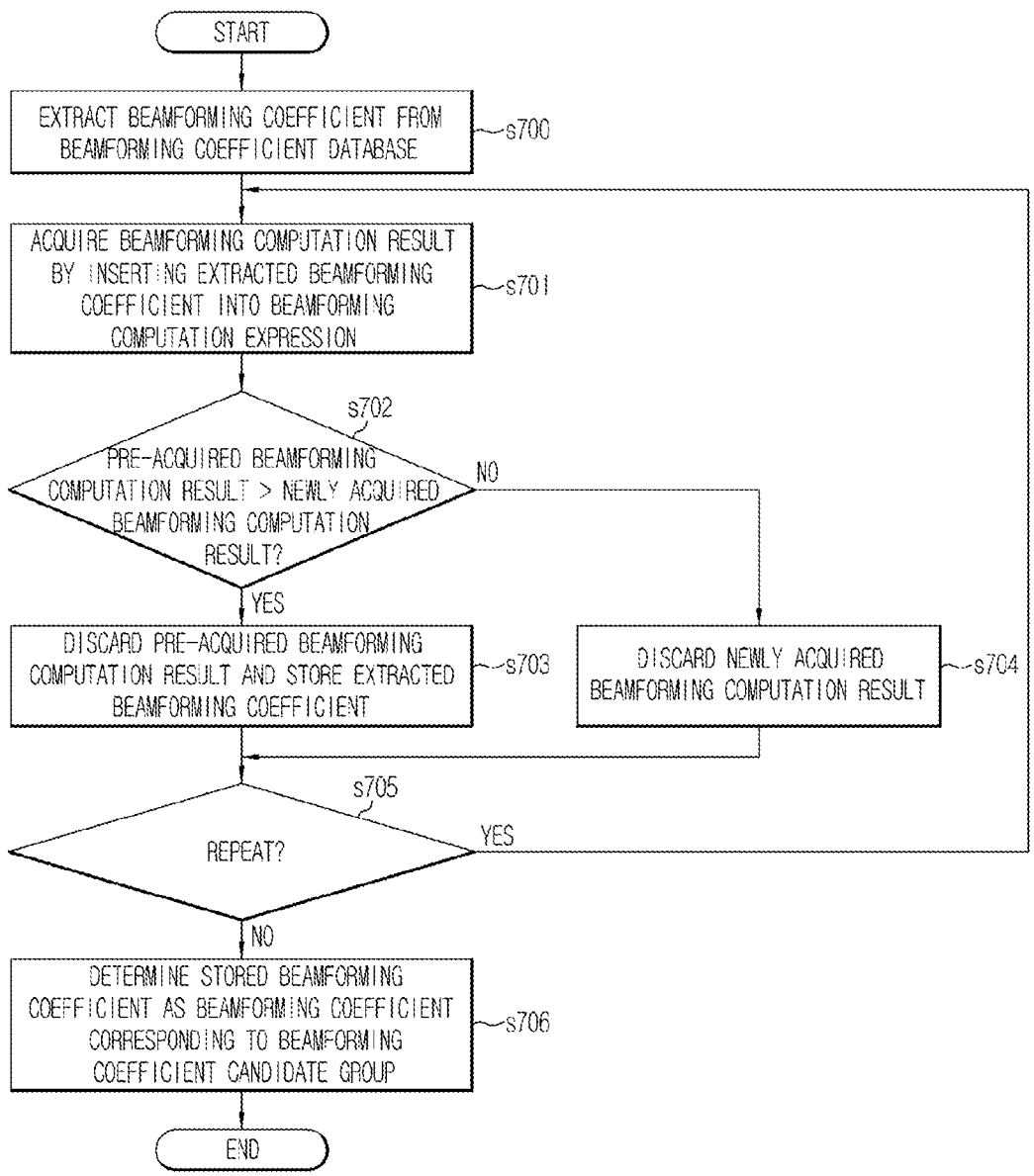
FIG. 11 is a flowchart of a method of determining a beamforming coefficient candidate group according to an embodiment of the present invention.

FIG. 11 is a flowchart of a method of determining a beamforming coefficient candidate group according to an embodiment of the present invention.

As shown in FIG. 11, in the method of determining a beamforming coefficient candidate group according to the present embodiment, first, a beamforming coefficient may be extracted from a beamforming coefficient database (s700).

Then, the extracted beamforming coefficient is inserted into a beamforming computation expression for determining a beamforming coefficient, for example, Expression 1 through Expression 4 above to acquire a beamforming computation result (s701).

Then, a pre-acquired beamforming computation result and a newly acquired beamforming computation result are compared to determine which result is greater (s702).

As a comparison result, when the pre-acquired beamforming computation result is greater than the newly acquired beamforming computation result, the pre-acquired beamforming coefficient is discarded and the newly extracted beamforming coefficient is stored (s703). When the pre-acquired beamforming computation result is less than the newly acquired beamforming computation result, the newly extracted beamforming coefficient is discarded and the pre-acquired beamforming coefficient is retained (s704).

Then, the aforementioned operations s701 through s704 are repeated a predetermined number of times to determine a finally stored beamforming coefficient, that is, a beamforming coefficient for optimization of a beamforming computation result as a beamforming coefficient corresponding to a beamforming coefficient candidate group (s705 through s706).

Accordingly, the beamforming coefficient candidate group may be determined.

Figure 12:
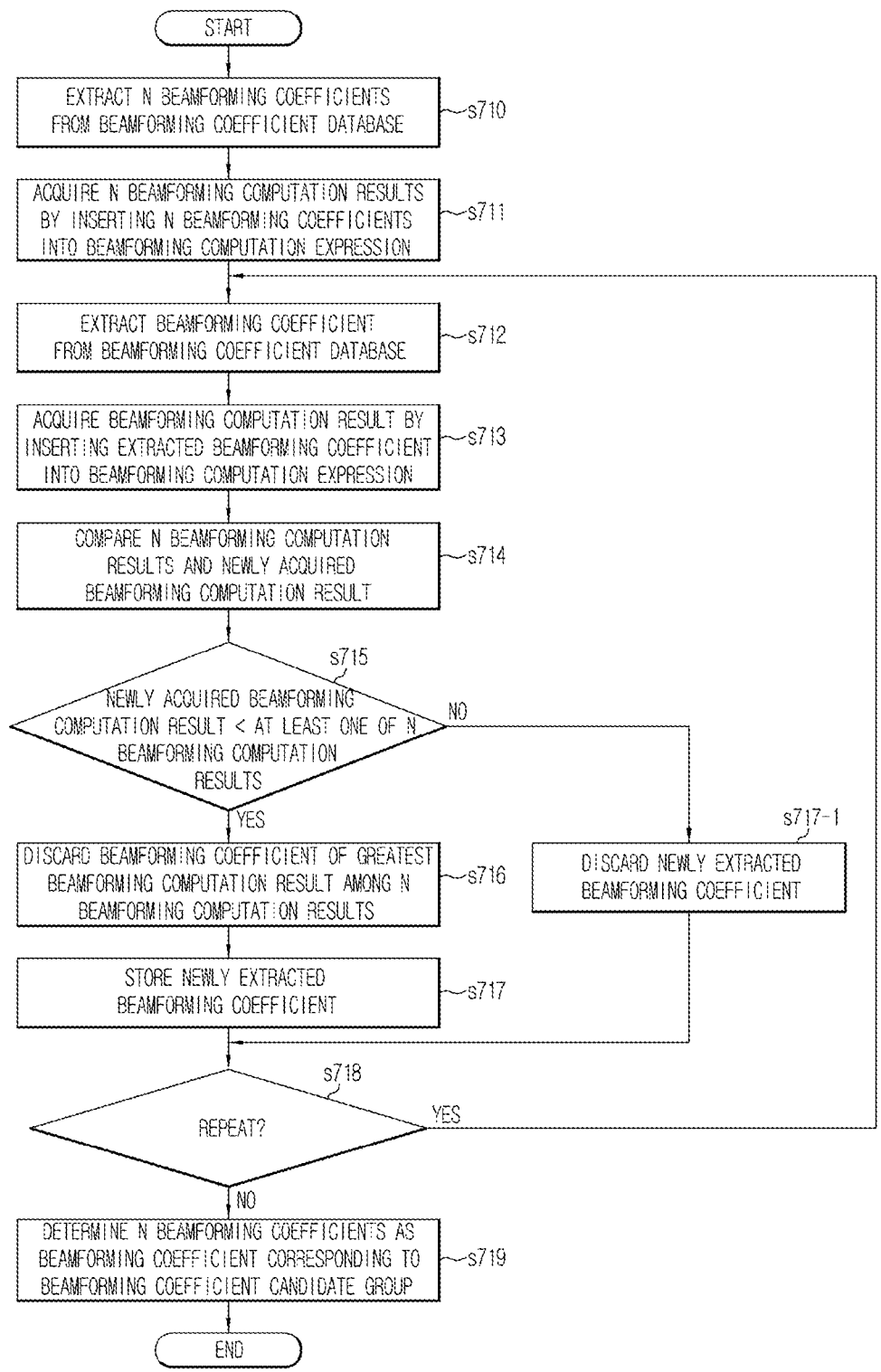
FIG. 12 is a flowchart of a method of determining a beamforming coefficient candidate group according to another embodiment of the present invention.

FIG. 12 is a flowchart of a method of determining a beamforming coefficient candidate group according to another embodiment of the present invention.

As shown in FIG. 12, in the method of determining a beamforming coefficient candidate group according to the present embodiment, first, N beamforming coefficients may be extracted from a beamforming coefficient database (s710).

Then, the beamforming coefficient computation unit 200 inserts the N beamforming coefficients into a beamforming computation expression, for example, at least one of Expression 1 through Expression 4 above to acquire N beamforming computation results (s711).

Then, the beamforming coefficient computation unit 200 extracts a beamforming coefficient from the beamforming coefficient database 300 (s712) and inserts the extracted beamforming coefficient into a beamforming computation expression, for example, any one of preset expressions such as Expression 1 through Expression 4 above (in general, the same as in operation s711) to acquire a beamforming computation result of the extracted beamforming coefficient (s713).

Then, the N beamforming computation results acquired in operation s711 and the new beamforming computation result acquired in operations s712 and s713 are compared with each other (s714) and it is determined whether the newly acquired beamforming computation result is less than at least one of the predetermined N beamforming computation results (s715).

As a determination result, when the new beamforming computation result acquired in operations s712 and s713 is less than at least one of the N beamforming computation results predetermined in operation s711, a beamforming coefficient of the greatest beamforming computation result among the N beamforming computation results may be discarded (s716), and the newly extracted beamforming coefficient may be stored instead of the discarded beamforming coefficient (s717).

When the new beamforming computation result acquired in operations s712 and s713 is greater than each of the N beamforming computation results predetermined in operation s711, the newly extracted beamforming coefficient is discarded and the N existing beamforming computation results are retained (s717-1).

Then, a new beamforming coefficient is further extracted from the beamforming coefficient database 300 to determine whether or not the aforementioned operations s712 through s717 are repeated. If it is determined that operations s712 through s717 are repeated, then operations s712 through s717 are repeated (s718). If it is determined that operations s712 through s717 are not repeated, that is, when a new beamforming coefficient is not extracted from the beamforming coefficient database 300, then N final beamforming coefficients acquired in operations s712 through s717-1 may be determined as a beamforming coefficient corresponding to a beamforming coefficient candidate group (s719).

Accordingly, the beamforming coefficient candidate group may be determined.

Hereinafter, a beamforming method will be described with regard to various embodiments of the present invention.

Figure 13:
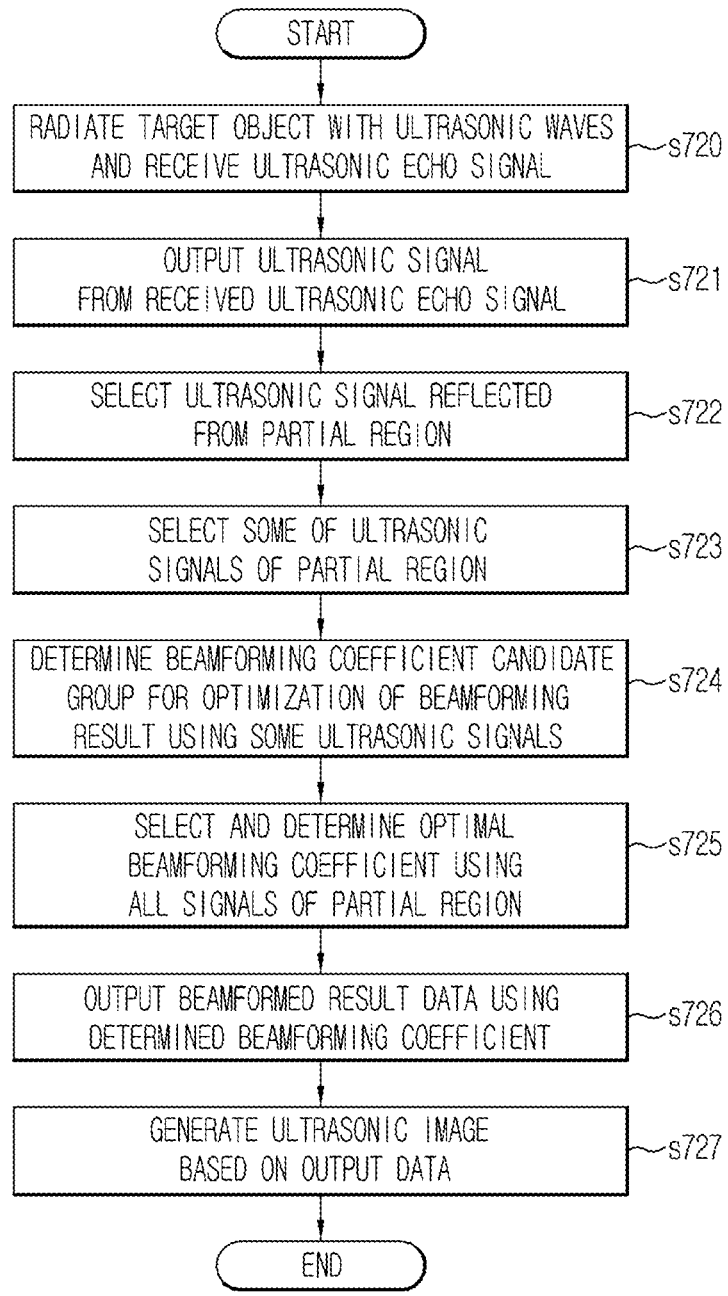
FIG. 13 is a beamforming method according to another embodiment of the present invention.

FIG. 13 is a beamforming method according to another embodiment of the present invention.

Referring to FIG. 13, in the beamforming method according to the present embodiment, first, a target object is radiated with ultrasonic waves and an ultrasonic echo signal is received (s720) and ultrasonic signals are output from the received ultrasonic echo signal (s721).

Ultrasonic signals reflected from predetermined partial regions of the target object ob are selected from the output ultrasonic signals (s722). Here, the predetermined partial regions may be preset from an entire region to be displayed as an ultrasonic image or may be selected by a user.

The beamforming coefficient computation unit 200 selects some of the ultrasonic signals of the partial regions that are preset or selected by the user (s723) and determines a beamforming coefficient candidate group for optimization of a beamforming result using the selected ultrasonic signals (s724).

The beamforming coefficient computation unit 200 selects and determines an optimal beamforming coefficient from the beamforming coefficient candidate group using all or some of the ultrasonic signals of the partial regions that are preset or selected by the user (s725).

The beamforming unit 100 performs beamforming on the selected regions that are preset or selected by the user using the beamforming coefficient determined in operations s720 through s725. Further, the beamforming unit 100 performs beamforming on other regions different from the selected regions using a beamforming coefficient determined using a different method from a case of operations s720 through s725, for example, a conventional method of determining a beamforming coefficient. Then, beamforming result data is output and transmitted to the image processor 400 (s726).

The image processor 400 generates an ultrasonic image based on the output data to display the ultrasonic image to the user (s727).

By virtue of the above method, beamforming according to the present embodiment is performed on a predetermined region of interest of an ultrasonic image, and a different beamforming method, for example, a conventional beamforming method is performed on other regions such that a partial region of the ultrasonic image and the other regions may be differentially processed.

Figure 14:
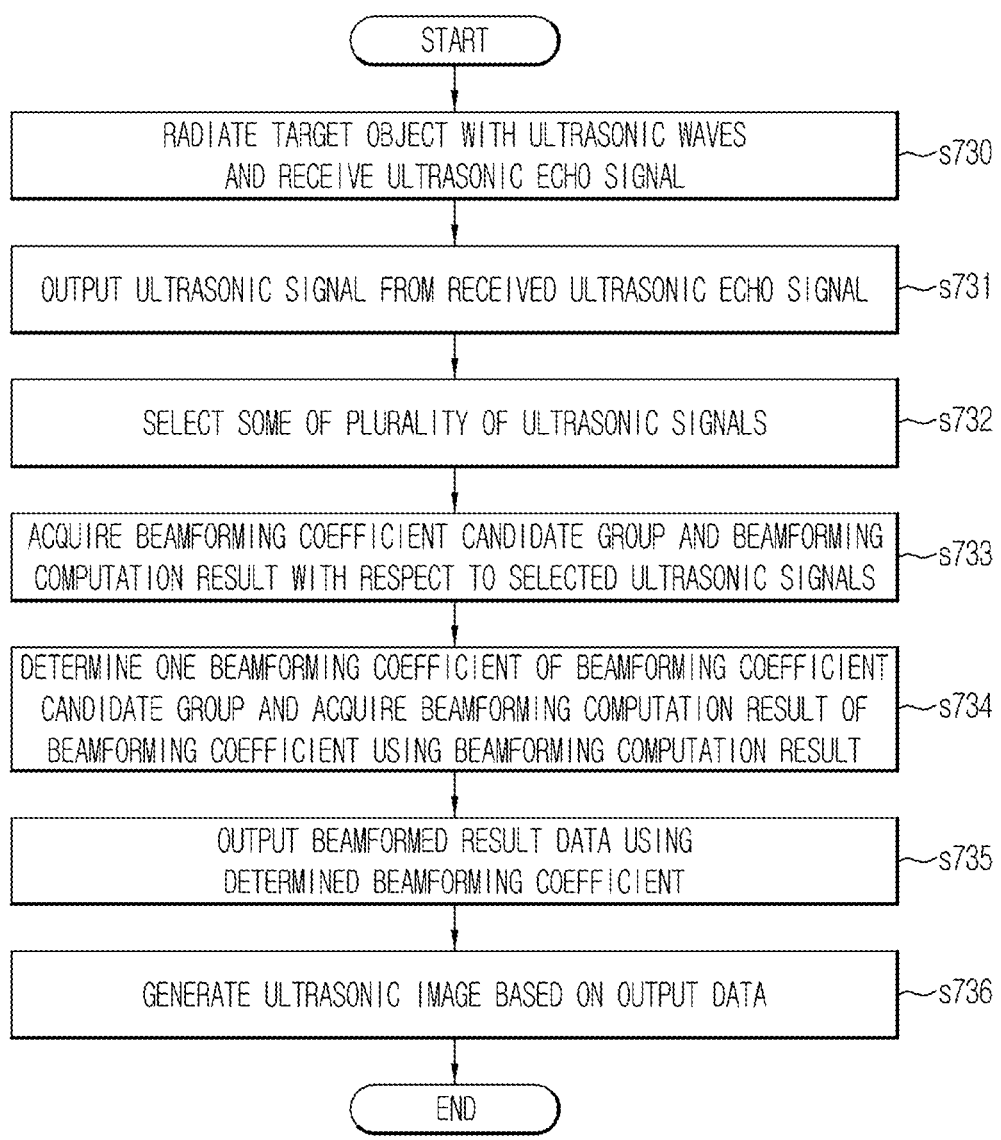
FIG. 14 is a flowchart of a beamforming method according to another embodiment of the present invention.

FIG. 14 is a flowchart of a beamforming method according to another embodiment of the present invention.

Referring to FIG. 14, in the beamforming method according to the present embodiment, first, ultrasonic waves are radiated to a target object and an ultrasonic echo signal is received (s730). Then a plurality of ultrasonic signals are output according to the received ultrasonic echo signal and transmitted to the beamforming coefficient computation unit 200 (s731).

The beamforming coefficient computation unit 200 may select some of the plurality of ultrasonic signals according to a predetermined condition (s732).

The beamforming coefficient computation unit 200 determines a beamforming coefficient candidate group of the selected ultrasonic signals using the aforementioned method, that is, the method using one of the Expression 1 through Expression 4 above, and acquires a beamforming computation result using the aforementioned method, that is, the method using one of the Expression 5 through Expression 8 above (s733).

Then, the beamforming coefficient computation unit 200 determines at least one beamforming coefficient to be used for beamforming from a beamforming coefficient candidate group using, for example, Expression 9 and Expression 11 through Expression 13 above, and acquires a beamforming computation result of a final determined beamforming coefficient using a beamforming computation result based on, for example, Expression 5 through Expression 8 above (s734). In this case, according to embodiments of the present invention, for example, Expression 14, Expression 15 through Expression 17 above, and the like may be used to acquire a beamforming computation result of a final beamforming coefficient.

Then, the beamforming unit 100 performs beamforming on an ultrasonic signal using the determined beamforming coefficient and outputs beamforming result data of the ultrasonic signal (s735).

The image processor 400 generates an ultrasonic image based on the output beamforming result data (s736).

(4) Thus, when a beamforming coefficient is determined to perform beamforming using the determined beamforming coefficient according to the embodiments of the present invention, the computational load may be significantly reduced compared with a other beamforming methods, in particular, the adaptive beamforming methods.

A beamforming method according to the embodiments of the preset invention is compared below with other adaptive beamforming methods such as a capon beamforming method and a full search beamforming method.

A multiplication number for the capon beamforming method is determined as a cube of the number of reception ultrasonic channels M (a for the capon beamforming method=M^3). A multiplication number for full search beamforming method is determined as P*(2K+1)*M. Here, P is the size of a beamforming coefficient database, that is, the number of beamforming coefficients stored in the database, K is an axial smoothing coefficient, and M is the number of channels.

In the method according to the embodiments of the present invention, a multiplication number may be determined according to Expression 18 below.

$$P \times (2K_{coarse}+1) \times M_{coarse} + N \times 2K_{fine} \times M_{fine} \qquad \text{[Expression 18]}$$

In Expression 18 above, it is assumed that P, the number of types of beamforming windows, that is, a size of a database or the number of beamforming coefficients, is 100; N, the number of beamforming coefficients of a beamforming coefficient candidate group is 10; M, the number of channels is 128; $M_{coarse}$ is 64; and $M_{fine}$ is the same as $M_{coarse}$. In addition, it is assumed that an axial smoothing coefficient K=15, $K_{coarse}$=1, and $K_{fine}$=$K_{coarse}$.

Thus, the computation load for acquiring one beamforming coefficient is determined as shown in Table 1 below with respect to the beamforming method according to the embodiments of the present invention, the capon beamforming method, and the full search beamforming method.

TABLE 1

|  | Capon beamforming method | Full search beamforming method | Embodiment of the present invention |
|---|---|---|---|
| Computational number | 2,097,152 | 396,800 | 37,120 |

As seen from Table 1 above, in the beamforming method according to the embodiments of the present invention, computational load is reduced to about 1/56 of the computational load corresponding to capon beamforming method. Further, in the beamforming method according to the embodiments of the present invention, computational load is reduced to about 1/10 of the computational load corresponding to the full search beamforming method. Thus, according to the present embodiment, a computational load for beamforming coefficients required for beamforming may be remarkably reduced.

As is apparent from the above description, a method of determining a beamforming coefficient, a beamforming method, and an ultrasonic imaging apparatus may be provided to reduce computational load in a process for acquiring beamforming coefficients.

Thus, in particular, when an adaptive beamforming method is used, a time for a beamforming process may be reduced, in other words, the beamforming process may be performed at high speed.

In addition, time delay, overload, overheating, or the like due to an excessive number of computations of various apparatuses for performing beamforming, for example, an ultrasonic imaging apparatus may be prevented.

The aspects of the invention in this application are not limited to the disclosed operations and sequence of operations. For instance, operations may be performed by various elements and components, may be consolidated, may be omitted, and may be altered without departing from the spirit and scope of the present invention.

Although a few embodiments of the present invention have been shown and described, it would be appreciated by those skilled in the art that changes may be made in these embodiments without departing from the principles and spirit of the invention, the scope of which is defined in the claims and their equivalents.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A beamforming method comprising:
   radiating a target object with ultrasonic waves and receiving a plurality of ultrasonic signals reflected from the target object by a total number M of transducers, the total number M being a natural number;
   acquiring first beamforming computation results for a first group of ultrasonic signals, among the received plurality of ultrasonic signals, wherein a number n of ultrasonic signals included into the first group is smaller than M;
   determining a beamforming coefficient candidate group based on the first beamforming computation results;
   acquiring second beamforming computation results for all or some of the received plurality of ultrasonic signals by applying beamforming coefficients of the beamforming coefficient candidate group;
   selecting a final beamforming coefficient from the beamforming coefficients of the beamforming coefficient candidate group based on the second beamforming computation results; and
   beamforming the received plurality of ultrasonic signals using the selected final beamforming coefficient as a weight.

2. The beamforming method according to claim 1, wherein the determining the beamforming coefficient candidate group comprises:
   extracting a plurality of beamforming coefficients from a beamforming coefficient database; and
   determining the beamforming coefficient candidate group by using the extracted plurality of beamforming coefficients.

3. The beamforming method according to claim 1, wherein the determining the beamforming coefficient candidate group comprises:
   selecting a plurality of beamforming coefficients stored in a database;
   determining the first beamforming computation results corresponding to the selected beamforming coefficients;
   comparing the determined first beamforming computation results with each other;
   selecting the beamforming coefficients of the beamforming coefficient candidate group, from the plurality of beamforming coefficients, such that:
      the beamforming coefficients selected in the beamforming coefficient candidate group have a variance which is smaller than a variance of the beamforming coefficients not selected in the beamforming coefficient candidate group.

4. The beamforming method according to claim 1, wherein the first beamforming computation results are beamforming computation results for the first group of ultrasonic signals, among the received plurality of ultrasonic signals, that are reflected from a partial region of the target object.

5. The beamforming method according to claim 1, wherein the first beamforming computation results are beamforming computation results obtained by performing smoothing on all or some of the received plurality of ultrasonic signals.

6. The beamforming method according to claim 1, further comprising:
   correcting a time difference of the received plurality of ultrasonic signals.

7. The beamforming method according to claim 1, wherein the acquiring the second beamforming computation results comprises acquiring the second beamforming computation results for a second group of ultrasonic signals, among the received plurality of ultrasonic signals, and the second group of ultrasonic signals includes ultrasonic signals different from those included into the first group.

8. A beamforming method comprising:
radiating a target object with ultrasonic waves and receiving a plurality of ultrasonic signals reflected from the target object;
acquiring first beamforming computation results for a first group of ultrasonic signals, among the received plurality of ultrasonic signals;
determining a beamforming coefficient candidate group based on the first beamforming computation results;
acquiring second beamforming computation results for all or some of the received plurality of ultrasonic signals by applying beamforming coefficients of the beamforming coefficient candidate group;
selecting a final beamforming coefficient from the beamforming coefficients of the beamforming coefficient candidate group based on the second beamforming computation results, and
beamforming coefficient as a weight,
wherein a beamforming coefficient included in the beamforming coefficient candidate group is calculated according to Expression 1 or Expression 2 below:

$$\{w_c\} = \underset{N\text{-best } w_p}{\operatorname{argmin}} \sum_{k=-K_{coarse}}^{k=K_{coarse}} \left| \sum_{i \in A1} w_p[i] x_{n+k}[i] \right|, \quad \text{[Expression 1]}$$

and $$\{w_c\} = \underset{N\text{-best } w_p}{\operatorname{argmin}} \sum_{k=-K_{coarse}}^{k=K_{coarse}} \left| \sum_{i \in A1} w_p[i] x_{n+k}[i] \right|^2, \quad \text{[Expression 2]}$$

where:
$W_c$ is the beamforming coefficient included in the beamforming coefficient candidate group,
$W_p[i]$ is a pre-stored beamforming coefficient,
$x_{n+k}[i]$ is an ultrasonic signal,
p is a beamforming coefficient index,
M is the number of reception ultrasonic channels,
i is a first channel index and $i \in A1$, where A1 is a sub-set of the set A={n: n is integer and $1 \le n \le M$};
"N-best" is the number of beamforming coefficients included in the beamforming coefficient candidate group,
k is an axial smoothing variable, and
$K_{coarse}$ is an upper or lower limit of the smoothing variable for acquisition of a plurality of beamforming coefficients for optimization of the first beamforming computation results.

9. The beamforming method according to claim 8, wherein the first channel index i belongs to the subset A1 ($i \in A1$) and:
A1={n: n is an odd integer number and $1 \le n \le M$}; or
A1={n: n is an even integer number and $1 \le n \le M$}.

10. The beamforming method according to claim 8, wherein the selecting the final beamforming coefficient from the beamforming coefficient candidate group comprises selecting a beamforming coefficient according to Expression 3 or Expression 4 below:

$$\{w_f\} = \underset{w_c}{\operatorname{argmin}} \left[ S_c(w_c^{(n)}) + \sum_{k \notin K_{coarse}} \left| \sum_{j \in A2} w_c^{(n)}[j] x_{n+k}[j] \right| \right], \quad \text{[Expression 3]}$$

and $$\{w_f\} = \underset{w_c}{\operatorname{argmin}} \left[ S_c(w_c^{(n)}) + \sum_{k \notin K_{coarse}} \left| \sum_{j \in A2} w_c^{(n)}[j] x_{n+k}[j] \right|^2 \right], \quad \text{[Expression 4]}$$

where:
$W_f$ is the selected beamforming coefficient,
j is a second channel index and $j \in A2$, where A2 is a sub-set of the set A, $A1 \cap A2 = \emptyset$; and
$S_c(w^{(n)}_c)$ is a beamforming computation result of an $n_{th}$ coefficient $w^{(n)}_c$ of the determined beamforming coefficient $W_c$.

11. The beamforming method according to claim 10, wherein the second channel index j belongs to the subset A2 ($j \in A2$) and:
A2={n: n is an even integer number and $1 \le n \le M$}; or
A2={n: n is an odd integer number and $1 \le n \le M$}.

12. The beamforming method according to claim 10, wherein the beamforming computation result $S_c(w^{(n)}_c)$ is determined as a result value $S_c$ of Expression 5 or Expression 6 below regarding an $n_{th}$ coefficient $w^{(n)}_c$ among determined beamforming coefficients $W_c$:

$$\{S_c\} = \underset{N\text{-best } w_p}{\min} \sum_{k=-K_{coarse}}^{k=K_{coarse}} \left| \sum_{i \in A1} w_p[i] x_{n+k}[i] \right|, \quad \text{[Expression 5]}$$

and $$\{S_c\} = \underset{N\text{-best } w_p}{\min} \sum_{k=-K_{coarse}}^{k=K_{coarse}} \left| \sum_{i \in A1} w_p[i] x_{n+k}[i] \right|^2. \quad \text{[Expression 6]}$$

* * * * *